United States Patent
Whitten et al.

(10) Patent No.: US 10,092,000 B2
(45) Date of Patent: Oct. 9, 2018

(54) STRUCTURE, SYNTHESIS, AND APPLICATIONS FOR OLIGO PHENYLENE ETHYNYLENES (OPES)

(75) Inventors: David G. Whitten, Albuquerque, NM (US); Kirk S. Schanze, Gainesville, FL (US); Eunkyung Ji, Ervy le Chatel (FR); Thomas S. Corbitt, Albuquerque, NM (US); Zhijun Zhou, Albuquerque, NM (US); Dimitri Dascier, Ervy le Chatel (FR); Ying Wang, Albuquerque, NM (US); Linnea K. Ista, Albuquerque, NM (US); Anand Parthasarathy, Naperville, IL (US); Eric H. Hill, Donostia (ES); Yanli Tang, Xi'an (CN)

(73) Assignees: STC.UNM, Albuquerque, NM (US); University of Florida Research Foundation, Inc., Gainesville, FL (US)

( * ) Notice: Subject to any disclaimer, the term of this patent is extended or adjusted under 35 U.S.C. 154(b) by 874 days.

(21) Appl. No.: 13/809,573

(22) PCT Filed: Jul. 13, 2011

(86) PCT No.: PCT/US2011/043908
§ 371 (c)(1),
(2), (4) Date: Mar. 6, 2013

(87) PCT Pub. No.: WO2012/009472
PCT Pub. Date: Jan. 19, 2012

(65) Prior Publication Data
US 2013/0273800 A1    Oct. 17, 2013

Related U.S. Application Data

(60) Provisional application No. 61/399,483, filed on Jul. 13, 2010, provisional application No. 61/400,122, (Continued)

(51) Int. Cl.
*A01N 43/90*    (2006.01)
*A01N 25/08*    (2006.01)
(Continued)

(52) U.S. Cl.
CPC ............. *A01N 43/90* (2013.01); *A01N 25/08* (2013.01); *A01N 25/10* (2013.01); *A01N 33/10* (2013.01);
(Continued)

(58) Field of Classification Search
None
See application file for complete search history.

(56) References Cited

U.S. PATENT DOCUMENTS

| 4,251,386 A | 2/1981 | Saeki et al. |
| 5,449,809 A | 9/1995 | Wingert et al. |

(Continued)

FOREIGN PATENT DOCUMENTS

| CA | 2973982 | 4/2018 |
| JP | 3198365 B2 | 11/1994 |

(Continued)

OTHER PUBLICATIONS

Wang et al., Membrane Perturbation Activity of Cationic Phenylene Ethynylene Oligomers and Polymers: Selectivity against Model Bacterial Mammalian Membranes, Jun. 29, 2010.*

(Continued)

*Primary Examiner* — Shawn Mckinnon
(74) *Attorney, Agent, or Firm* — Schwegman Lundberg & Woessner, P.A.

(57) ABSTRACT

The present disclosure provides novel oligo phenylene ethynylene (OPE) compounds, methods for synthesizing these compounds, and materials and substances incorporating
(Continued)

these compounds. The various OPEs show antibacterial, antiviral and antifungal activity.

22 Claims, 16 Drawing Sheets

Related U.S. Application Data filed on Jul. 22, 2010, provisional application No. 61/366,850, filed on Jul. 22, 2010, provisional application No. 61/401,825, filed on Aug. 19, 2010, provisional application No. 61/401,832, filed on Aug. 19, 2010, provisional application No. 61/404,236, filed on Sep. 29, 2010, provisional application No. 61/456,552, filed on Nov. 8, 2010, provisional application No. 61/413,878, filed on Nov. 15, 2010, provisional application No. 61/471,800, filed on Apr. 5, 2011, provisional application No. 61/499,097, filed on Jun. 20, 2011.

(51) Int. Cl.

| | | |
|---|---|---|
| *A01N 43/10* | (2006.01) | |
| *A01N 33/12* | (2006.01) | |
| *A01N 33/10* | (2006.01) | |
| *A01N 41/04* | (2006.01) | |
| *A01N 25/10* | (2006.01) | |
| *C07D 487/08* | (2006.01) | |
| *C07C 309/11* | (2006.01) | |
| *C07C 217/20* | (2006.01) | |
| *C07D 333/16* | (2006.01) | |
| *C07D 409/14* | (2006.01) | |

(52) U.S. Cl.
CPC ............. *A01N 33/12* (2013.01); *A01N 41/04* (2013.01); *A01N 43/10* (2013.01); *C07C 217/20* (2013.01); *C07C 309/11* (2013.01); *C07D 333/16* (2013.01); *C07D 409/14* (2013.01); *C07D 487/08* (2013.01); *Y10T 442/30* (2015.04)

(56) References Cited

U.S. PATENT DOCUMENTS

| | | | |
|---|---|---|---|
| 5,489,400 | A | 2/1996 | Liu et al. |
| 6,743,640 | B2 | 6/2004 | Whitten et al. |
| 6,841,669 | B2 | 1/2005 | Cipriani et al. |
| 7,122,383 | B2 | 10/2006 | Jones et al. |
| 8,455,265 | B2 | 6/2013 | Whitten et al. |
| 8,598,053 | B2 | 12/2013 | Whitten et al. |
| 8,618,009 | B2 | 12/2013 | Schanze et al. |
| 8,753,570 | B2 | 6/2014 | Whitten et al. |
| 9,005,540 | B2 | 4/2015 | Schanze et al. |
| 9,125,415 | B2 | 9/2015 | Schanze et al. |
| 9,527,806 | B2 | 12/2016 | Whitten et al. |
| 9,549,549 | B2 | 1/2017 | Whitten et al. |
| 2002/0177828 | A1 | 11/2002 | Batich et al. |
| 2003/0134959 | A1 | 7/2003 | Hancock et al. |
| 2003/0168756 | A1 | 9/2003 | Kenneth, Jr. et al. |
| 2003/0178607 | A1 | 9/2003 | Swager et al. |
| 2004/0241768 | A1 | 12/2004 | Whitten et al. |
| 2005/0059168 | A1 | 3/2005 | Bazan et al. |
| 2005/0148254 | A1 | 7/2005 | Lu et al. |
| 2006/0120923 | A1 | 6/2006 | Swager et al. |
| 2006/0175193 | A1 | 8/2006 | Inganas et al. |
| 2007/0065049 | A1 | 3/2007 | Alldredge-howard et al. |
| 2007/0215841 | A1 | 9/2007 | Ford et al. |
| 2008/0090021 | A1 | 4/2008 | Long et al. |
| 2010/0035948 | A1 | 2/2010 | Kumar et al. |
| 2010/0285081 | A1 | 11/2010 | Chen et al. |
| 2011/0076648 | A1 | 3/2011 | Lindheim et al. |
| 2011/0159605 | A1 | 6/2011 | Whitten et al. |
| 2011/0223058 | A1 | 9/2011 | Whitten et al. |
| 2011/0293470 | A1 | 12/2011 | Schanze et al. |
| 2012/0271023 | A1 | 10/2012 | Whitten et al. |
| 2013/0210828 | A1 | 8/2013 | Whitten et al. |
| 2013/0330386 | A1 | 12/2013 | Whitten et al. |
| 2014/0086795 | A1 | 3/2014 | Schanze et al. |
| 2014/0242148 | A1 | 8/2014 | Whitten et al. |
| 2014/0341776 | A1 | 11/2014 | Schanze et al. |
| 2015/0115362 | A1 | 4/2015 | Su et al. |
| 2015/0132184 | A1 | 5/2015 | Whitten et al. |
| 2016/0222150 | A1 | 8/2016 | Whitten et al. |
| 2017/0023554 | A1 | 1/2017 | Whitten et al. |
| 2017/0057970 | A1 | 3/2017 | Whitten et al. |
| 2017/0164614 | A1 | 6/2017 | Whitten et al. |
| 2018/0020663 | A1 | 1/2018 | Whitten et al. |

FOREIGN PATENT DOCUMENTS

| | | |
|---|---|---|
| WO | 2005065323 | 7/2005 |
| WO | WO-2008/143731 A2 | 11/2008 |
| WO | WO-2009/158606 A2 | 12/2009 |
| WO | WO-2009158606 A9 | 12/2009 |
| WO | WO-2010/044743 A1 | 4/2010 |
| WO | WO-2010/054304 A2 | 5/2010 |
| WO | 2011044580 | 4/2011 |
| WO | WO-2011/044580 A3 | 4/2011 |
| WO | WO-2012/009484 A2 | 1/2012 |
| WO | WO-2012009472 A2 | 1/2012 |
| WO | WO-2012/079085 A2 | 6/2012 |
| WO | WO-2013/020096 A2 | 2/2013 |
| WO | WO-2013/020096 A3 | 2/2013 |
| WO | WO-2013/055417 A2 | 4/2013 |
| WO | WO-2013/055417 A3 | 4/2013 |
| WO | WO-2015138965 A1 | 9/2015 |
| WO | WO-2016115362 A1 | 7/2016 |

OTHER PUBLICATIONS

Zhinjou, Zhou, Studies of a cyanine-based biosensor and light-induced antibacterial activities of oligo phenylene ethynylenes, Feb. 9, 2011.*

U.S. Appl. No. 12/529,390, filed May 13, 2010, Surface Grafted Conjugated Polymers, U.S. Pat. No. 8,455,265.

U.S. Appl. No. 13/503,067, filed Jul. 13, 2012, Materials Incorporating Antimicrobial Polymers, U.S. Pat. No. 8,598,053.

U.S. Appl. No. 13/001,478, filed May 11, 2011, Structure, Synthesis, and Applications for Oligo Phenylene Ethynlenes, U.S. Pat. No. 8,753,570.

U.S. Appl. No. 13/128,571, filed Aug. 8, 2011, Conjugated Polyelectrolyte capsules: Light Activated Antimicrobials, U.S. Pat. No. 8,618,009.

U.S. Appl. No. 14/092,409, filed Nov. 27, 2013, Conjugated Polyelectrolyte Capsules: Light Activated Antimicrobials, U.S. Pat. No. 9,005,540.

U.S. Appl. No. 13/993,026, filed Aug. 29, 2013, Structure, Synthesis, and Applications for Conjugated Polyampholytes.

U.S. Appl. No. 14/233,130, filed May 8, 2014, Antimicrobial Materials and Methods.

U.S. Appl. No. 13/809,572, filed Apr. 3, 2013, Structure, Synthesis, and Applications for Poly (Phenylene) Ethynylenes (PPEs).

U.S. Appl. No. 14/127,465, filed May 7, 2014, Thiophene Based Oligomers as Light Activated Biocides, U.S. Pat. No. 9,125,415.

U.S. Appl. No. 14/533,612, filed Nov. 5, 2014, Charged Singlet-Oxygen Sensitizers and Oppositely-Charged Surfactants.

PubChem. Substance Record for SID 76464254. Retrieved from the Internet. <URL: https://pubchem.ncbi.nlm.nih.gov/substance/76464254#section=Top>, (Jun. 12, 2009).

"U.S. Appl. No. 12/529,390, Examiner Interview Summary dated Jan. 31, 2012", 3 pgs.

"U.S. Appl. No. 12/529,390, Examiner Interview Summary dated Nov. 13, 2012", 18 pgs.

"U.S. Appl. No. 12/529,390, Non Final Office Action dated Jul. 18, 2012", 8 pgs.

(56) References Cited

OTHER PUBLICATIONS

"U.S. Appl. No. 12/529,390, Non-Final Office Action dated Nov. 1, 2011", 11 pgs.
"U.S. Appl. No. 12/529,390, Notice of Allowance dated Feb. 5, 2013", 10 pgs.
"U.S. Appl. No. 12/529,390, Preliminary Amendment dated Sep. 1, 2009", 13 pgs.
"U.S. Appl. No. 12/529,390, Response filed May 1, 2012 to Non Final Office Action dated Nov. 1, 2011", 19 pgs.
"U.S. Appl. No. 12/529,390, Response filed Dec. 18, 2012 to Non Final Office Action dated Jul. 18, 2012", 16 pgs.
"U.S. Appl. No. 13/001,478 , Response filed Dec. 19, 2013 to Non Final Office Action dated Oct. 3, 2013", 10 pgs.
"U.S. Appl. No. 13/001,478, Non Final Office Action dated Oct. 3, 2013", 7 pgs.
"U.S. Appl. No. 13/001,478, Notice of Allowance dated Jan. 31, 2014", 7 pgs.
"U.S. Appl. No. 13/001,478, Response filed Jul. 11, 2013 to Restriction Requirement dated Jun. 13, 2013", 9 pgs.
"U.S. Appl. No. 13/001,478, Restriction Requirement dated Jun. 13, 2013", 7 pgs.
"U.S. Appl. No. 13/128,571, Response filed May 13, 2013 to Non Final Office Action dated Feb. 13, 2013", 12 pgs.
"U.S. Appl. No. 13/128,571, Response filed Nov. 19, 2012 to Restriction Requirement dated Oct. 17, 2012", 6 pgs.
"U.S. Appl. No. 13/128,571, Non Final Office Action dated Feb. 13, 2013", 10 pgs.
"U.S. Appl. No. 13/128,571, Notice of Allowance dated Aug. 28, 2013", 9 pgs.
"U.S. Appl. No. 13/128,571, Preliminary Amendment filed May 10, 2011", 5 pgs.
"U.S. Appl. No. 13/128,571, Restriction Requirement dated Oct. 17, 2012", 6 pgs.
"U.S. Appl. No. 13/503,067 , Response filed Mar. 11, 2013 to Non Final Office Action dated Oct. 10, 2012", 11 pgs.
"U.S. Appl. No. 13/503,067 , Response filed Jul. 11, 2013 to Final Office Action dated Jun. 6, 2013", 7 pgs.
"U.S. Appl. No. 13/503,067, Final Office Action dated Jun. 6, 2013", 11 pgs.
"U.S. Appl. No. 13/503,067, Non Final Office Action dated Oct. 10, 2012", 11 pgs.
"U.S. Appl. No. 13/503,067, Notice of Allowance dated Aug. 2, 2013", 10 pgs.
"U.S. Appl. No. 13/993,026 Response filed Sep. 8, 2015 to Final Office Action dated Jun. 8, 2015", 10 pgs.
"U.S. Appl. No. 13/993,026, Final Office Action dated Jun. 8, 2015", 15 pgs.
"U.S. Appl. No. 13/993,026, Non Final Office Action dated Jan. 27, 2015", 9 pgs.
"U.S. Appl. No. 13/993,026, Preliminary Amendment filed Jun. 10, 2013", 7 pgs.
"U.S. Appl. No. 13/993,026, Response filed Apr. 9, 2015 to Non Final Office Action dated Jan. 27, 2015", Response to Non Final Office Action, 11 pgs.
"U.S. Appl. No. 14/092,409, Notice of Allowance dated Dec. 10, 2014", 10 pgs.
"U.S. Appl. No. 14/127,465, Non Final Office Action dated Jan. 21, 2015", 4 pgs.
"U.S. Appl. No. 14/127,465, Notice of Allowance dated Apr. 30, 2015", 7 pgs.
"U.S. Appl. No. 14/127,465, Response filed Apr. 20, 2015 to Non Final Office Action dated Jan. 21, 2015", 9 pgs.
"U.S. Appl. No. 14/533,612, Notice of Publication mailed", 1 pg.
"European Application Serial No. 09771137.8, Office Action dated Feb. 9, 2011", 1 pg.
"European Application Serial No. 09771137.8, Office Action dated Feb. 14, 2011", 2 pgs.
"European Application Serial No. 09771137.8, Office Action dated Mar. 3, 2011", 1 pg.
"European Application Serial No. 09771137.8, Office Action dated Mar. 16, 2011", 1 pg.
"European Application Serial No. 09771137.8, Response filed Feb. 18, 2011 to Office Action dated Feb. 9, 2011", 6 pgs.
"International Application Serial No. PCT/US2008/002756, International Preliminary Report on Patentability dated Sep. 1, 2009", 6 pgs.
"International Application Serial No. PCT/US2008/002756, International Search Report dated Feb. 25, 2009", 2 pgs.
International Application Serial No. PCT/US2008/002756, Written Opinion dated Feb. 25, 2009, 5 pgs.
"International Application Serial No. PCT/US2009/048838, International Preliminary Report on Patentability dated Jan. 5, 2011", 7 pgs.
"International Application Serial No. PCT/US2009/048838, International Search Report dated Apr. 30, 2010", 4 pgs.
"International Application Serial No. PCT/US2009/048838, Written Opinion dated Apr. 30, 2010", 6 pgs.
"International Application Serial No. PCT/US2009/063715, International Preliminary Report on Patentability dated May 10, 2011", 6 pgs.
"International Application Serial No. PCT/US2009/063715, International Search Report dated May 27, 2010", 4 pgs.
"International Application Serial No. PCT/US2009/063715, Written Opinion dated May 27, 2010", 5 pgs.
"International Application Serial No. PCT/US2010/052332, International Preliminary Report on Patentability dated Apr. 11, 2012", 7 pgs.
"International Application Serial No. PCT/US2010/052332, International Search Report dated Jun. 24, 2011", 4 pgs.
"International Application Serial No. PCT/US2010/052332, Written Opinion dated Jun. 24, 2011", 6 pgs.
"International Application Serial No. PCT/US2011/043922, International Preliminary Report on Patentability dated Jan. 15, 2013", 4 pgs.
"International Application Serial No. PCT/US2011/043922, International Search Report dated Mar. 19, 2012", 3 pgs.
"International Application Serial No. PCT/US2011/043922, Written Opinion dated Mar. 19, 2012", 3 pgs.
"International Application Serial No. PCT/US2011/064460, International Preliminary Report on Patentability dated Jun. 20, 2013", 7 pgs.
"International Application Serial No. PCT/US2011/064460, International Search Report dated Jun. 19, 2012", 6 pgs.
"International Application Serial No. PCT/US2011/064460, Written Opinion dated Jun. 19, 2012", 5 pgs.
"International Application Serial No. PCT/US2012/045598, International Preliminary Report on Patentability dated Jan. 23, 2014", 6 pgs.
"International Application Serial No. PCT/US2012/045598, International Search Report dated May 27, 2013", 3 pgs.
"International Application Serial No. PCT/US2012/045598, Written Opinion dated May 27, 2013", 4 pgs.
"International Application Serial No. PCT/US2012/049613, International Preliminary Report on Patentability dated Feb. 13, 2014", 9 pgs.
"International Application Serial No. PCT/US2012/049613, International Search Report dated Feb. 26, 2013", 3 pgs.
"International Application Serial No. PCT/US2012/049613, Written Opinion dated Feb. 26, 2013", 7 pgs.
"International Application Serial No. PCT/US2015/020546, International Search Report dated Aug. 10, 2015", 4 pgs.
"International Application Serial No. PCT/US2015/020546, Invitation to Pay Additional Fees and Partial Search Report dated May 20, 2015", 2 pgs.
"International Application Serial No. PCT/US2015/020546, Written Opinion dated Aug. 10, 2015", 5 pgs.
Ambade, A.V, et al., "Fluorescent Polyelectrolytes as Protein Sensors", In: Polym. Int., 2007, vol. 56, (2007), 474-481.
Antoci, Jr., Valentin, et al., "Vancomycin covalently bonded to titanium alloy prevents bacterial colonization", Journal of Orthopaedic Research, 25(7), (2007), 858-866.

(56) References Cited

OTHER PUBLICATIONS

Arnt, Lachelle, et al., "Cationic Facially Amphiphilic Poly(phenylene ethynylene)s Studied at the Air-Water Interface", Langmuir, 19(6), (2004), 2404-2408.

Arnt, Lachelle, et al., "New Poly(phenyleneethynylene)s with Cationic, Facially Amphiphilic Structures", Journal of the American Chemical Society,124(26), (2002), 7664-7665.

Arnt, Lachelle, et al., "Nonhemolytic Abiogenic Polymers as Antimicrobial Peptide Mimics", J. Polym. Sci., Part A: Polym. Chem., 42(15), (2004), 3860-3864.

Bartlett, Grant R., "Phosphorus Assay in Column Chromatography", The Journal of Biological Chemistry, 234(3), (1959), 466-468.

Beaujuge, Pierre M., et al., "Spectral Engineering in pie-Conjugated Polymers with Intramolecular Donor-Acceptor Interactions", Accounts of Chemical Research, 43(11), (Nov. 2010), 1396-1407.

Beckloff, Nicholas, et al., "Activity of an Antimicrobial Peptide Mimetic against Planktonic and Biofilm Cultures of Oral Pathogens", Antimicrobial Agents and Chemotherapy, 51, (2007), 4125-4132.

Capuano, Ben, et al., "The Synthesis and Preliminary Pharmacological Evaluation of a Series of Substituted 4'-Phenoxypropyl Analogues of the Atypical Antipsychotic Clozapine", Aust. J. Chem., 63, (2010), 116-124.

Ceri, H., et al., "The Calgary Biofilm Device: New Technology for Rapid Determination of Antibiotic Susceptibilities of Bacterial Biofilms", Journal of Clinical Microbiology, 37(6), (1999), 1771-1776.

Chemburu, Sireesha, et al., "Light-Induced Biocidal Action of Conjugated Polyelectrolytes Supported on Colloids", Langmuir, 24, (2008), 11053-11062.

Choi, W. S., et al., "Synthesis of Two Types of Nanoparticles in Polyelectrolyte Capsule Nanoreactors and Their Dual Functionality", J. Am. Chem. Soc., 127, (2005), 16136-16142.

Clark, A. P. Z., et al., "An Amphiphilic Poly(phenylene ethynylene) as the Structure-Directing Agent for Periodic Nanoscale Silica Composite Materials", Nano Letters, 5, (2005), 1647-1652.

Corbitt, Thomas, et al., "Antimicrobial Non-Woven Fibrous Materials", U.S. Appl. No. 61/528,603, filed Aug. 29, 2011, 17 pgs.

Corbitt, Thomas S., et al., "Light and dark biocidal activity of cationic poly(arylene ethynylene) conjugated polyelectrolytes", Photochem. Photobiol. Sci., 8, (2009), 998-1005

Costerton, J. William, et al., "Mechanism of Electrical Enhancement of Efficacy of Antibiotics in Killing Biofilm Bacteria", Antimicrobial Agents and Chemotherapy, 38(12), (1994), 2803-2809.

Dascier, Dimitri, et al., "Efficacy of End-Only-Functionalized Oligo(arylene-ethynylene)s in Killing Bacterial Biofilms", Langmuir, 28(31), (2012), 11286-11290.

De Geest, B. G., et al., "Release mechanisms for polyelectrolyte capsules", Chem. Soc. Rev., 36, (2007), 636-649.

Ding, Liping, et al., "Insight into the Mechanism of Antimicrobial Poly(phenylene ethynylene) Polyelectrolytes: Interactions with Phosphatidylglycerol Lipid Membranes", Langmuir, 25(24), (2009), 13742-13751.

Donlan, Rodney M., et al., "Microbial Life on Surfaces", Emerging Infectious Diseases, 8(9), (2002), 881-890.

Eun, Ye-Jin, et al., "Fabrication of Microbial Biofilm Arrays by Geometric Control of Cell Adhesion", Langmuir, 25(8), (2009), 4643-4654.

Fan, Qu-Li, et al., "Water-Soluble Cationic Poly(p-phenyleneethynylene)s (PPEs): Effects of Acidity and Ionic Strength on Optical Behavior.", Macromolecules.vol. 38, 2927-2936

Fang, Zhen, et al., "Low-Bandgap Donor-Acceptor Conjugated Polymer Sensitizers for Dye-Sensitized Solar Cells", Journal of the American Chemical Society, 133(9), (2011), 3063-3069.

Ferreira, Isabel C.F.R, et al., "Screening of antimicrobial activity of diarylamines in the 2,3,5-trimethylbenzo[b]thiophene series a structure-activity evaluation study", Bioorganic & Medicinal Chemistry Letters, 14(23), (2004), 5831-5833.

Gao, Yuan, et al., "Recent Advances in Antimicrobial Treatments of Textiles", Textile Research Journal vol. 78(1), 60-72.

Gao, Yuan, et al., "Recent Advances in Antimicrobial tTeatment of Textiles", Textile Research Journal, 78(1), (2008), 60-72

George, Wayne N., et al., "Amplified fluorescence quenching in high ionic strength media.", Soft Matter. vol. 3, (2007), 1381-1387.

Guan, Bin, et al., "Different Functionalization of the Internal and External Surfaces in Mesoporous Materials for Biosensing Applications Using "Click" Chemistry", Langmuir, 27(1), (2010), 328-334.

Harrison, Joe J., et al., "Microtiter susceptibility testing of microbes growing on peg lids: a miniaturized biofilm model for high-throughput screening", Nature Protocols, 5(7), (2010), 1236-1254.

Hortholary, Cedric, et al., "An Approach to Long and Unsubstituted Molecular Wires:? Synthesis of Redox-Active, Cationic Phenylethynyl Oligomers Designed for Self-Assembled Monolayers", J. Org. Chem., 68(6), (2003), 2167-2174.

Huisgen, Rolf, "Centenary Lecture—1,3-Dipolar Cycloadditions", Proceedings of the Chemical Society of London, (Oct. 1961), 357-369.

Ibraeva, Zhanar E., et al., "Solution Properties and Complexation of Polyampholytes based on N,N-Dimethyldiallyl-ammonium Chloride and Maleic Acid or Alkyl (Aryl) Derivatives of Malemic Acids", Macromol. Chem. Phys., 205, (2004), 2464-2472.

Ista, Linnea K., et al., "Conjugated-Polyelectrolyte-Grafted Cotton Fibers Act as "Micro Flypaper" for the Removal and Destruction of Bacteria", ACS Applied Materials & Interfaces, 3(8), (2011), 2932-2937.

Ji, E., "Conjugated polyelectrolytes: Synthesis, photophysical studies and applications to sensors and biocidal activity", Ph.D. dissertation, Univ. of Florida, 2009, (2009), 167 pgs.

Ji, E., et al., "pH-Dependent Optical Properties of a Poly(phenylene ethynylene) Conjugated Polyampholyte", In: Langmuir, vol. 27, (Dec. 28, 2010), 1565-1568.

Ji, Eunkyung, et al., "Antibacterial Activity of Conjugated Polyelectrolytes with Variable Chain Lengths", Langmuir, 27, (2011), 10763-10769.

Ji, Eunkyung, et al., "Light and Dark-Activated Biocidal Activity of Conjugated Polyelectrolytes", ACS Applied Materials & Interfaces, 3(8), (2011), 2820-2829.

Jiang, Hui, et al., "Conjugated Polyelectrolytes: Synthesis, Photophysics, and Applications", Angew. Chem. Int. Ed., 48(24), (2009), 4300-4316.

Jiang, Hui, et al., "Effects of Polymer Aggregation and Quencher Size on Amplified Fluorescence Quenching of Conjugated Polyelectrolytes", Langmuir, 23(18), (2007), 9381-9486.

Kenawy, El-Refaie, et al., "The Chemistry and Applications of Antimicrobial Polymers: A State-of-the-Art Review", Biomacromolecules, 8(5), (2007), 1359-1384.

Kim, Chae Kyu, et al., "Complexation of Anionic Conjugated Polyelectrolyte with Cationic Surfactant", Macromolecular Research, vol. 13 No. 5, (Oct. 31, 2005), 460-462.

Kolb, Hartmuth C., et al., "Click Chemistry: Diverse Chemical Function from a Few Good Reactions", Angew. Chem. Int. Ed., 40, (2001), 2004-2021

Kotz, Joachim, "Inter- and intramolecular interactions in polyelectrolyte complex formation with polyampholytes", Macromolecular Chemistry and Physics, 194(2), (1993), 397-410.

Leach, Michelle K., et al., "Electrospinning Fundamentals: Optimizing Solution and Apparatus Parameters", Journal of Visualized Experiments, 47, (2011), 4 pgs.

Lee, H., et al., "Shell Cross-Linked Hyaluronic Acid/Polylysine Layer-by-Layer Polyelectrolyte Microcapsules Prepared by Removal of Reducible Hyaluronic Acid Microgel Cores", Biomacromolecules, 8, (2007), 3705-3711.

Lee, Wen-Fu, et al., "Synthesis and solubility of the poly(sulfobetaine)s and the corresponding cationic polymers: 2. Aqueous solution properties of poly[ N,N'-dimethyl-(acrylamido propyl) ammonium propane sulfonate]", Polymer, 36(2), (1995), 357-364.

Lindsay, D., et al., "Bacterial biofilms within the clinical setting: what healthcare professionals should know", Journal of Hospital Infection, 64, (2006), 313-325.

(56) References Cited

OTHER PUBLICATIONS

Liu, Yan, et al., "Conjugated polyelectrolytes as fluorescent sensors", Journal of Photochemistry and Photobiology C: Photochemistry Reviews, 10(4), (2009), 173-190.

Lowe, Andrew B., et al., "Synthesis and Solution Properties of Zwitterionic Polymers", Chem. Rev., 102, (2002), 4177-4189.

Lu, L., et al., "Biocidal Activity of a Light-Absorbing Fluorescent Conjugated Polyelectrolyte", Langmuir, 21, (2005), 10154-10159.

Lu, Timothy K., et al., "Dispersing biofilms with engineered enzymatic bacteriophage", Proc. Natl. Acad. Sci. USA, 104(27), (2007), 11197-11202.

McCormick, C. L., "Polyampholytes (Overview)", In: Polymeric Materials Encyclopedia, vol. 7, CRC Press, Boca Raton, FL, (1996), 5462-5476.

McQuade, D. Tyler, et al., "Signal Amplification of a Turn-On Sensor: Harvesting the Light Captured by a Conjugated Polymer", J. Am. Chem, Soc., 122, (2000), 12389-12390.

Notestein, Justin M., et al., "Covalent Grafting of m-Phenylene-Ethynylene Oligomers to Oxide Surfaces", Chem. Mater., 22, (2010), 5319-5327.

Olson, Merle E., et al., "Biofilm bacteria: formation and comparative susceptibility to antibiotics", Canadian Journal of Veterinary Research—Revue Canadienne De Recherche Veterinaire, 66, (2002), 86-92.

Pasquier, Nicolas, et al., "From Multifunctionalized poly(ethylene Imine)s toward Antimicrobial Coatings", Biomacromolecules, 8, (2007), 2874-2882.

Patel, Dinesh G., et al., "It Takes More Than an Imine: The Role of the Central Atom on the Electron-Accepting Abilitty of Benzotriazole and Benzothiadiazole Oligomers", Journal of the American Chemical Society, 134(5), (2012), 2599-2612.

Pinto, Mauricio R., et al., "Amplified fluorescence sensing of protease activity with conjugated polyelectrolytes", Proc. Natl. Acad. Sci. USA, 101(20), (2004), 7505-7510.

Pinto, Mauricio R., et al., "Conjugated Polyelectrolytes: Synthesis and Applications", Synthesis, 9, (2002), 1293-1309.

Potera, Carol, "C. Microbiology—Forging a Link Between Biofilms and Disease", Science, 283(5409), (1999), 1837-1939.

Reddinger, Jerry L., et al., "Molecular Engineering of p-Conjugated Polymers", Radical Polymerisation Polyelectrolytes, Series: Advances in Polymer Science, vol. 145, (1999), 57-122.

Schanze, K. S, et al., "Functional Polyelectrolytes", In: Langmuir, 2009, vol. 25, (2009), 13698-13702.

Schlüter, A. D., "The Tenth Anniversary of Suzuki Polycondensation (SPC)", Journal of Polymer Science Part A: Polymer Chemistry, 39(10), (2001), 1533-1556.

Senthilkumar, Sadasivam, et al., "Photophysical properties of coumarin-30 dye in aprotic and protic solvents of varying polarities", Photochemistry and Photobiology, 80, (2004), 104-111.

Shi, Songqing, et al., "Synthesis and Characterization of a Water-Soluble Poly(p-phenylenevinylene) Derivative", Macromolecules, 23(8), (1990), 2119-2124.

Stewart, Philip S., et al., "Physiological heterogeneity in biofilms", Nature Reviews Microbiology, 6, (Mar. 2008), 199-210.

Tan, C, et al., "Photophysics, aggregation and amplified quenching of a water-soluble poly(phenylene ethynylene)", Chem. Commun., (2002), 446-447.

Tan, C., et al., "Solvent-induced Self-Assembly of a Meta-Linked Conjugated Polyelectrolyte. Helix Formation. Guest Intercalation, and Amplified Quenching", Adv. Mater., vol. 16, No. 14, (2004), 1208-1212.

Tan, Chunyan, et al., "Amplified Quenching of a Conjugated Polyelectrolyte by Cyanine Dyes", J. Am. Chem. Soc., 126, (2004), 13685-13694.

Tan, Chunyan, et al., "Photophysics, aggregation and amplified quenching of a water-soluble poly(phenylene ethynylene)", Chem. Commun., (2002), 446-447.

Tan, Chunyan, et al., "Solvent-Induced Self-Assembly of a Meta-Linked Conjugated Polyelectrolyte. Helix Formation, Guest Intercalation, and Amplified Quenching", Advanced Materials, 16(14), with Supporting Materials, (2004), 1208-1212 (16 pgs.).

Tang, Yanli, et al., "Light-induced antibacterial activity of symmetrical and asymmetrical oligophenylene ethynylenes", Langmuir, 27(8), (2011), 4956-4962.

Tang, Yanli, et al., "Synthesis, Self-Assembly, and Photophysical Properties of Cationic Oligo(p-phenyleneethynylene)s", Langmuir, 27(8), (2011), 4945-4955.

Tew, G. N, et al., Biochimica et Biophysica Acta 2006, (2006), 1387-1392.

Thomas, III, Samuel W., et al., "Chemical Sensors Based on Amplifying Fluorescent Conjugated Polymers", Chem. Rev., 107, (2007), 1339-1386.

Tiller, J. C., et al., "Designing surfaces that kill bacteria on contact", Proc. Natl. Acad, Sci. USA, 98(11), (May 22, 2001), 5981-5985.

Tong, W., et al., "Single Polyelectrolyte Microcapsules Fabricated by Glutaraldehyde-Mediated Covalent Layer-By-Layer Assembly", Macromol. Rapid Commun., 27, (2006), 2078-2083.

Valle, Jaione, et al., "Broad-spectrum biofilm inhibition by a secreted bacterial polysaccharide", Proc. Natl. Acad. Sci. USA, 103(33), (2006), 12558-12563.

Wallow, Thomas I., et al., "In Aqua Synthesis of Water-Soluble Poly(p-phenylene) Derivatives", J. Am. Chem. Soc., 113, (1991), 7411-7412.

Wang, Deli, et al., "Biosensors from conjugated polyelectrolyte complexes", Proc. Natl. Acad. Sci. USA, 96, (1999), 12287.

Wang, Deli, et al., "Photoluminescence Quenching of Conjugated Macromolecules by Bipyridinium Derivatives in Aqueous Media: Charge Dependence", Langmuir, 17, (2001), 1262-1266.

Wang, Ying, et al., "Direct Visualization of Bactericidal Action of Cationic Conjugated Polyelectrolytes and Oligomers", Langmuir, 28, (2012), 65-70.

Wang, Yingsheng, et al., "Photochemical probes of intramolecular electronc and energy transfer", Chemical Physics, 176, (1993), 305-319.

Wang, Z., et al., "Preparation and application of single polyelectrolyte microcapsules possessing tunable autofluorescent properties.", Colloids and Surfaces A: Physicochemical and Engineering Aspects, 329, (2008), 58-66.

Xu, Shimei, et al., "Effect of the Anionic-Group/Cationic-Group Ratio on the Swelling Behavior and Controlled Release of Agrochemicals of the Amphoteric, Superabsorbent Polymer Poly(acrylic acid-co-diallyldimethylammonium chloride)", Journal of Applied Polymer Science, 102, (2006), 986-991.

Yang, Chaoyong James, et al., "Direct Synthesis of an Oligonucleotide-Poly-(phenylene ethynylene) Conjugate with a Precise One-to-One Molecular Ratio", Angew. Chem. Int. Ed. 44, (2005), 2572-2576.

Zhang, Lian-Hui, et al., "Quorum sensing and signal interference: diverse implications", Molecular Microbiology, 53(6), (2004), 1563-1571.

Zhao, Xiaoyong, et al., "Varible Band Gap Poly(arylene ethynylene) Conjugated Polyelectrolytes", Macromolecules, 39, (2006), 6355-6366.

Zhao, Xiaoyong, et al., "Varible Bsnd Gap Poly(arylene ethynylene) Conjugated Polyelectrolytes", Macromolecules, 39, (2006), 6355-6366.

Zhou, Zhijun, et al., "End-Only Functionalized Oligo(phenylene ethynylene)s: Synthesis, Photophysical and Biocidal Activity", Journal of Physical Chemistry Letters, 1(21), (2010), 3207-3212.

Zhu, Huiguang, et al., "Synthesis of Size-Controlled Monodisperse Manganese Carbonate Microparticles as Templates for Uniform Polyelectrolyte Microcapsule Formation.", Chern. Mater.,17, (2005), 2323-2328.

"International Application Serial No. PCT/US2011/043908, International Preliminary Report on Patentability dated Jan. 15, 2013", 7 pgs.

Bruns, R., et al., "Chapter 3—R&D in material protection: New biocides", In: Directory of Microbicides for the Protection of Materials—A Handbook, Paulus, W., Editor, (2005), 25-46.

Corbitt, Thomas S., et al., "Conjugated Polyelectrolyte Capsules: Light-Activated Antimicrobial Micro "Roach Motels"†", ACS Appl. Mater. Interfaces, 1(1), (2009), 48-52.

(56) References Cited

OTHER PUBLICATIONS

Galaev, Igor Y., "'Smart' polymers in biotechnology and medicine", *Russian Chemical Reviews*, 64(5) (1995), 471-489.

Hoffman, Allan S., "Bioconjugates of Intelligent Polymers and Recognition Proteins for Use in Diagnostics and Affinity Separations", *Clinical Chemistry*, 46:9, (2000), 1478-1486.

Lin, Ching-Yao, et al., "Design and Characterization of Novel Porphyrins with Oligo(phenylethylnyl) Links of Varied Length for Dye-Sensitized Solar Cells: Synthesis and Optical, Electrochemical, and Photovoltaic Investigation", *J. Phys. Chem. C.*, 113(2), (2009), 755-764.

Ogawa, Katsu, et al., "Conjugated Polyelectrolyte-Grafted Silica Microspheres", *Langmuir*, 23(8), (2007), 4541-4548.

Schild, H. G., "Poly(N-Isopropylacrylamide): Experiment, Theory and Application", *Prog. Polym. Sci.*, 17, (1992), 163-249.

"International Application Serial No. PCT/US2011/043908, International Search Report and Written Opinion dated Apr. 6, 2012", 11 pgs.

Tang, Yanli, et al., "Synthesis, Self-Assembly, and Photophysical Behavior of Oligo Phenylene Ethynylenes: From Molecular to Supramolecular Properties", Langmuir vol. 25, (2009), 21-25.

Wang, Ying, et al., "Membrane Perturbation Activity of Cationic Phenylene Ethynylene Oligomers and Polymers: Selectivity against Model Bacterial and Mammalian Membranes", Langmuir, 26(15), (Jun. 29, 2010), 12509-12514.

"U.S. Appl. No. 13/001,478, Preliminary Amendment filed Dec. 27, 2010", 1 pg.

"U.S. Appl. No. 13/128,571, Preliminary Amendment filed May 31, 2011", 3 pgs.

"U.S. Appl. No. 13/809,572, Final Office Action dated Feb. 18, 2016", 20 pgs.

"U.S. Appl. No. 13/809,572, Non Final Office Action dated Sep. 24, 2015", 17 pgs.

"U.S. Appl. No. 13/809,572, Preliminary Amendment filed Jan. 10, 2013".

"U.S. Appl. No. 13/809,572, Response filed Apr. 22, 2016 to Final Office Action dated Apr. 18, 2016", 9 pgs.

"U.S. Appl. No. 13/993,026, Advisory Action dated Sep. 17, 2015", 7 pgs.

"U.S. Appl. No. 14/092,409, Preliminary Amendment filed Nov. 25, 2014", 4 pgs.

"U.S. Appl. No. 14/092,409, Preliminary Amendment filed Dec. 3, 2013", 4 pgs.

"U.S. Appl. No. 14/127,465, Preliminary Amendment filed Dec. 18, 2013".

"U.S. Appl. No. 14/233,130, Preliminary Amendment filed Jan. 15, 2014", 11 pgs.

"U.S. Appl. No. 14/233,130, Response filed Dec. 10, 2015 to Restriction Requirement dated Oct. 22, 2015", 12 pgs.

"U.S. Appl. No. 14/233,130, Non Final Office Action dated Jan. 14, 2016", 14 pgs.

"U.S. Appl. No. 14/233,130, Response filed Apr. 1, 2016 to Non-Final Office Action dated Jan. 14, 2016", 14 pgs.

"U.S. Appl. No. 14/233,130, Restriction Requirement dated Oct. 22, 2015", 11 pgs.

"European Application Serial No. 09771137.8, Search Report dated Nov. 4, 2013", 6 pgs.

"International Application Serial No. PCT/US2016/013431, International Search Report dated Apr. 25, 2016", 3 pgs.

"International Application Serial No. PCT/US2016/013431, Written Opinion dated Apr. 25, 2016", 7 pgs.

Addinall, Stephen, et al., "Temperature Shift Experiments with an ftsZ84(Ts) Strain Reveal Rapid Dynamics of FtsZ Localization and Indicate hat the Z Ring is Required throughout Septation and Cannot Reoccupy Division Sites Once Constriction Has Initiated", J. of Bacteriology, vol. 179, No. 13, (1997), 4277-4284.

Anderson, David E, et al., "Assembly Dynamics of FtsZ Rings in *Bacillus subtilis* and *Escherichia coli* and Effects of FtsZ-Regulating Proteins", Journal of Bacteriology, 186(17)., (2004), 5775-5781.

Boeneman, Kelly, et al., "*Escherichia coli* DnaA forms helical structures along the longitudinal cell axis distinct from MreB ?laments", Molecular Microbiology, 72(3)., (2009), 645-657.

Buffet-Bataillon, Sylvie, et al., "Emergence of resistance to antibacterial agents: the role of quaternary ammonium compounds—a critical review", International Journal of Antimicrobial Agents, 39(5)., (2012), 381-389.

Burton, Paul, et al., "Two Pathways of Division Inhibition in UV-Irradiated *E. coli*", Mol Gen Genet., 190(1)., (1983), 128-132.

Cabiscol, Elisa, et al., "Oxidative stress in bacteria and protein damage by reactive oxygen species", International Microbiology, 3., (2000), 3-8.

Chamchod, Farida, et al., "Modeling methicillin-resistant *Staphylococcus aureus* in hospitals: Transmission dynamics, antibiotic usage and its history", Theor Biol Med Model. , 9, 25., (2012), 1-14.

Cooper, B S, et al., "Methicillin-resistant *Staphylococcus aureus* in hospitals and the community: Stealth dynamics and control catastrophes", Proc. Nat. Acad. Sci., 2004, 101(27)., (2004), 10223-10228.

Corbitt, et al., "Conjugated Polyelectrolyte Capsules: Light-Activated Antimicrobial Micro", Roach Motels Applied Materials and Interfaces vol. 1 No. 1, (Nov. 24, 2008), 48-52.

Cramton, Sarah, et al., "The Intercellular Adhesion (ica) Locus is Present in *Staphylococcus aureus* and is Required for Biofilm Formation", Infection and Immunity, 67(10)., (1999), 5427-5433.

Evans, D, et al., "Critical Micelle Concentrations for Alkyltrimethylammonium Bromides in Water from 25 to160° C.", J. Solution Chem., 13(2)., (1984), 87-101.

Flemming, Hans-Curt, et al., "The biofilm matrix", Nat Rev Microbiol., 8(9)., (2010), 623-633.

Gaylord, Brent, et al., "DNA Hybridization Detection with Water-Soluble Conjugated Polymers and Chromophore-Labeled Single-Stranded DNA", Journal of the American Chemical Society, vol. 125, No. 4, (Jan. 9, 2003), 896-900.

Gilbert, P, et al., "Biofilms in vitro and in vivo: do singular mechanism imply cross-resistance?", J Appl Microbiol.,92 Suppl., (2002), 98S-110S.

Goehring, Nathan, et al., "Diverse Paths to Midcell: Assembly of the Bacterial Cell Division Machinery", Current Biology, 15., (2005), R514-R526.

Gorwitz, R, et al., "More Challenges in the Prevention and Management of Community-Associated, Methicillin-Resistant *Staphylococcus aureus* Skin Disease", Ann. Intern. Med.,148 (4)., (2008), 310-312.

Hill, Eric, et al., "Cationic oligo-p-phenylene ethynylenes form complexes with surfactants for long-term light-activated biocidal applications", Photochem. Photobiol, Sci., 13., (2014), 247-253.

Hill, Eric, et al., "Molecular Dynamics Simulation Study of the Interaction of Cationic Biocides with Lipid Bilayers: Aggregation E?ects and Bilayer Damage", Langmuir 28, (2012), 14849-14854.

Hill, Eric, et al., "Photochemistry of "End-Only" Oligo-p-phenylene Ethynylenes: Complexation with Sodium Dodecyl Sulfate Reduces Solvent Accessibility", Langmuir, 29(31), (2013), 9712-9720.

Jones, Tineke, "Response of *Escherichia coli* to Environmental Stress", Stress Response of Foodborne Microorganisms. NovaScience Publishers., (2012), 293-330.

Kilger, Robert, et al., "Bidirectional energy transfer between the triplet T1 state of photofrin and singlet oxygen in deuterium oxide", Chemical Physics Letter 343, (2001), 543-548.

Kim, Sook Kyung, et al., "Chemosensors for Pyrophosphate", Accounts of Chemical Research 42, (2009), 23-31.

Klevens, R M, et al., "Estimating Health Care-Associated Infections and Deaths in U.S. Hospitals", Public Health Rep., 2007, 122(2)., (2002), 160-166.

Kruse, T, et al., "Dysfunctional MreB inhibits chromosome segregation in *Escherichia coli*", EMBO J., 22(19)., (2003), 5283-5292.

Leid, Jeff, et al., "Human Leukocytes Adhere to Penetrate, and Respond to *Staphylococcus aureus* Bioflms", Infection and Immunity, 70(11)., (2002), 6339-6345.

Lindig, Barbara, et al., "Determination of the Lifetime of Singlet Oxygen in D20 Using 9, IO-Anthracenedipropionic Acid, a Water-Soluble Probe", J. Am. Chem. Soc., 102 (17)., (1980), 5590-5593.

(56) References Cited

OTHER PUBLICATIONS

Liu, Yan, et al., "Conjugated Polyelectrolyte-Based Real-Time Fluorescence Assay for Alkaline Phosphatase with Pyrophosphate as Substrate", Anal. Chem. 80, (2008), 8605-8612.

Lock, Rowena, et al., "Cell-division inhibitors: new insights for Future anibiotics", Nature Reviews Drug Discovery, 7., (2008), 324-338.

Maciag-Dorszynska, Monika, et al., "Mutations in central carbon metabolism genes suppress defects in nucleoid position and cell division of replication mutants in *Escherichia coli*", Gene 503., (2012), 31-35.

Magrex-Debar, Elisabeth, et al., "Evaluation of biohazards in dehydrated bio?lms", International Journal of Food Microbiology 55., (2000), 239-243.

Mah, Thien-Fah, et al., "Mechanisms of biofilm resistance to antimicrobial agents", TRENDS in Microbiology vol. 9 No. 1., (2001), 34-39.

Maisch, Tim, et al., "The role of singlet oxygen and oxygen concentration in photodynamic inactivation of bacteria", The National Academy of Sciences of the USA. PNAS vol. 104, No. 17, (2007), 7223-7228.

Malik, Zvi, et al., "New Trends in Photobiology (Invited Review) Bactericidal Effects of Photoactivated Porphyrins—An Alternative Approach to Antimicrobial Drugs", Journal of Photochemistry and Photobiology B: Biology, 5(3-4)., (1990), 281-293.

Mann, Ethan, et al., "Modulation of eDNA Release and Degradation Affects *Staphylococcus aureus* Biofilm Maturation", PLOS One, 4(6)., (2009), e5822.

McNeill, Karol, et al., "Acid tolerance response of bio¢lm cells of *Streptococcus mutans*", FEMS Microbiology Letters, 221., (2003), 25-30.

Neuhaus, Francis, et al., "A Continuum of Anionic Charge: Structures and Functions of D-Alanyl-Teichoic Acids in Gram-Positive Bacteria", Microbiology and Molecular Biology Reviews, 67(4)., (2003), 686-723.

Nickerson, Emma, et al., "*Staphylococcus aureus* disease and drug resistance in resource-limited countries in south and east Asia", Lancet Infect, Dis., 9., (2009), 130-135.

Nikaido, Hiroshi, "Outer Membrane", *Escherichia coli* and *Salmonella*: cellular and molecular biology. 2nd ed. Washington, D.C: American Society for Microbiology., (1996), 29-47.

Parthasarathy, Anand, "Conjugated Polyelectrolytes with Imidazolium Solubilizing Groups Properties and Application to Photodynamic Inactivation of Bacteria", ACS Applied Materials & Interfaces vol. 7, No. 51, (2015), 28027-28034.

Pinto, Mauricio, et al., "Amplified fuorescence quenching and biosensor application of a poly (para-phenylene) cationic polyelectrolyte", Res. Chem. Intermed, 33, (2007), 79-90.

Rice, Kelly, et al., "The cidA murein hydrolase regulator contributes to DNA release and biofilm development in *Staphylococcus aureus*", Proc. Nat. Acad, Sci., 104(19)., (2007), 8113-8118.

Rico, Ana Isabel, et al., "Role of *Escherichia coli* FtsN protein in the assembly and stability of the cell division ring", Molecular Microbiology, 76(3)., (2010), 760-771.

Rolinson, George, "Forty years of β-lactam research", Journal of Antimicrobial Chemotherapy, 41., (1998), 589-603.

Romberg, Laura, et al., "Assembly Dynamics of the Bacterial Cell Division Protein FTSZ: Poised at the Edge of Stability", Annual Review of Microbiology, 57., (2003), 125-154.

Ron, Eliora, et al., "Growth Rate of *Escherichia coli* at Elevated Temperature: Lomitation by Methionine", Journal of Bacteriology, 107(1)., (1971,), 391-396.

Stewart, Philip, et al., "Antibiotic resistance of bacteria in biofilms", Lancet, 358., (2001), 135-138.

Storz, Gisela, et al., "Oxidative stress", Current Opinion in Microbiology, 2., (1999), 188-194.

Stricker, Jesse, et al., "Rapid assembly dynamics of the *Escherichia coli* FtsZ-ring demonstrated by fluorescence recovery after photobleaching", Proc. Nat. Acad. Sci., 99(5)., (2002), 3171-3175.

Tacconelli, Evelina, et al., "Does antibiotic exposure increase the risk of methicillin-resistant *Staphylococcus aureus* (MRSA) isolation? A systematic review and meta-analysis", J. Antimicrob, Chemother.,61(1)., (2008), 26-38.

Tan, et al., "Hyper-Efficient Quenching of a Conjugated Polyelectrolyte by Dye-Doped Silica Nanoparticles: Better Quenching in the Nonaggregated State", Langmuir Letter 26(3), (Nov. 19, 2009), 1528-1532.

Teitzel, Gail, "Heavy Metal Resistance of Bio?lm and Planktonic Pseudomonas aeruginosa", Applied and Environmental Microbiology, 69(4)., (2003), 2313-2320.

Trauble, Hermann, et al., "The Structure of *Escherichia coli* Membranes Studied by Fluorescence Measurement of Lipid Phase Transitions", Biophys. Acta, 307., (1973), 491-512.

Turro, J, et al., "Luminescent Probes for Detergent Solutions. A Simple Procedure for Determination of the Mean Aggregation Number of Micelles", J. Am. Chem. Soc., 100., (1978), 5951-5952.

Vollmer, Waldemar, et al., "Peptidoglycan structure and architecture", FEMS Microbiol. Rev. 32(2)., (2008), 149-167.

Wang, Ying, et al., "Understanding the Dark and Light-Enhanced Bactericidal Action of Cationic Conjugated Polyelectrolytes and Oligomers", Langmuir, 29(2)., (2013), 781-792.

Wosnick, Jordan H., et al., "Synthesis and Application of Poly(phenyleneEthynylene)s for Bioconjugation: A Conjugated Polymer-Based Fluorogenic Probe", American Chemical Society,127, (2005), 3400-3405.

Zhai, Lei, et al., "A Simple Method to Generate Side-Chain Derivatives of Regioregular Polythiophene via the GRIM Metathesis and Post-polymerization Functionalization", Macromolecules 36, (2003), 61-64.

Zhou, Zhijun, et al., ""End-Only" Functionalized Oligo (phenylene ethynylene) s: Synthesis, Photophysical and Biocidal Activity, J. Phys. Chem. Lett, 1., (2010), 3207-3212.

"U.S. Appl. No. 13/809,572, Notice of Allowance dated Aug. 10, 2016", 8 pgs.

"U.S. Appl. No. 14/233,130, Final Office Action dated Jun. 29, 2016", 16 pgs.

"U.S. Appl. No. 14/233,130, Notice of Allowance dated Sep. 12, 2016", 13 pgs.

"U.S. Appl. No. 14/233,130, Response filed Aug. 12, 2016 to Final Office Action dated Jun. 29, 2016", 13 pgs.

"U.S. Appl. No. 14/533,612, Restriction Requirement dated Aug. 25, 2016", 8 pgs.

"U.S. Appl. No. 15/018,179, Response filed Sep. 9, 2016 to Restriction Requirement dated Jul. 13, 2016", 15 pgs.

"U.S. Appl. No. 15/018,179, Restriction Requirement dated Jul. 13, 2016", 10 pgs.

U.S. Appl. No. 15/368,148, filed Dec. 2, 2016, Antimicrobial Materials and Methods.

U.S. Appl. No. 15/348,756, filed Nov. 10, 2016, Structure, Synthesis, and Applications for Poly (Phenylene) Ethynylenes (PPEs).

U.S. Appl. No. 15/125,896, filed Sep. 13, 2016, P-Phynylene Ethynylene Compounds as Bioactive and Detection Agents.

U.S. Appl. No. 15/668,390, filed Aug. 3, 2017, Conjugated Polyelectrolytes and Methods of Using the Same.

U.S. Appl. No. 61/399,483, filed Jul. 13, 2010.

U.S. Appl. No. 61/401,825, filed Aug. 19, 2010.

U.S. Appl. No. 61/404,236, filed Sep. 29, 2010.

U.S. Appl. No. 61/401,832, filed Aug. 19, 2010.

U.S. Appl. No. 61/400,122, filed Jul. 22, 2010.

U.S. Appl. No. 61/456,552, filed Nov. 8, 2010.

"U.S. Appl. No. 14/533,612, Final Office Action dated Jul. 13, 2017", 11 pgs.

"U.S. Appl. No. 14/533,612, Response filed Apr. 20, 2017 to Non-Final Office Action dated Jan. 20, 2017", 11 pgs.

"U.S. Appl. No. 15/018,179, Notice of Allowance dated May 3, 2017", 9 pgs.

"U.S. Appl. No. 15/348,756, Non Final Office Action dated Jun. 23, 2017", 26 pgs.

"U.S. Appl. No. 15/368,148, Non Final Office Action dated Jul. 6, 2017", 16 pgs.

"U.S. Appl. No. 15/368,148, Repsonse filed Jun. 12, 2017 to Restriction Requirement dated Apr. 12, 2017", 10 pgs.

(56) References Cited

OTHER PUBLICATIONS

"International Application Serial No. PCT/US2016/013431, International Preliminary Report on Patentability dated Jul. 27, 2017", 9 pgs.
Chemburu, et al., "Conjugated Polyelectrolyte Supported Bead Based Assays for Phospholipase A2 Activity", (2008), 14492-14499.
Narendiran, "Electrospun Ultrathin Nylon Fibers for Protective Applications", Journal of Applied Polymer Science, vol. 116, (Jan. 7, 2010), 2181-2187.
"U.S. Appl. No. 14/233,1330, 312 Amendment dated Nov. 11, 2016", 3 pgs.
"U.S. Appl. No. 15/125,896, Restriction Requirement dated Mar. 27, 2018", 6 pgs.
"U.S. Appl. No. 15/348,756, Non Final Office Action dated Mar. 9, 2018", 29 pgs.
"U.S. Appl. No. 15/348,756, Response filed Jan. 18, 2018 to Final Office Action dated Nov. 8, 2017", 10 pgs.
"U.S. Appl. No. 15/368,148, Notice of Allowance dated Jan. 30, 2018", 16 pgs.
"U.S. Appl. No. 15/368,148, Preliminary Amendment filed Dec. 2, 2016", 10 pgs.
"Japanese Application Serial No. 2017-554255, Office Action dated Jan. 9, 2018", with machine translation, 5 pgs.
Parthasarathy, Anand, et al., "Conjugated Polyelectrolytes with Imidazolium Solubilizing Groups, Properties and Application to Photodynamic Inactivation of Bacteria", ACS Appl. Mater. Interfaces, vol. 7, No. 51, (Jun. 16, 2015), 28027-28034.
"U.S. Appl. No. 14/533,612, Advisory Action dated Nov. 24, 2017", 5 pgs.
"U.S. Appl. No. 14/533,612, Advisory Action dated Nov. 24, 2017", 3 pgs.
"U.S. Appl. No. 14/533,612, Notice of Allowance dated Jan. 8, 2018". 8 pgs.
"U.S. Appl. No. 14/533,612, Response filed Dec. 12, 2017 to Final Office Action dated Jul. 13, 2017", 16 pgs.
"U.S. Appl. No. 13/809,572, Amendment 312 filed Oct. 21, 2016", 5 pgs.
"U.S. Appl. No. 14/233,130, PTO Response to Rule 312 Communication dated Dec. 8, 2016", 2 pgs.
"U.S. Appl. No. 14/533,612, Non Final Office Action dated Jan. 20, 2017", 11 pgs.
"U.S. Appl. No. 14/533,612, Response filed Oct. 11, 2016 to Restriction Requirement dated Aug. 25, 2016", 8 pgs.
"U.S. Appl. No. 15/018,179, Non Final Office Action dated Dec. 13, 2016", 12 pgs.
"U.S. Appl. No. 15/018,179, Response filed Mar. 10, 2017 to Non-Final Office Action dated Dec. 13, 2016", 13 pgs.
"U.S. Appl. No. 15/125,896, Preliminary Amendment dated Sep. 13, 2016", 11 pgs.
"U.S. Appl. No. 15/348,756, Preliminary Amendment filed Nov. 18, 2016 to", 7 pgs.
"U.S. Appl. No. 15/368,148, Restriction Requirement dated Apr. 12, 2017", 11 pgs.
Tan, et al., "Thermodynamics of Sodium Dodecyl Sulfate Partitioning into Lipid Membranes", Biophysics Journal vol. 83, (2002), 1547-1556 pgs.
"Japanese Application Serial No. 2017-554255, Response filed Apr. 3, 2018 to Office Action dated Jan. 9, 2018", (W English Claims), 17 pgs.
"European Application Serial No. 16737889.2, Extended European Search Report dated Mar. 21, 2018", 7 pgs.
"Japanese Application Serial No. 2017-554255, Office Action dated Apr. 17, 2018", w English translation, 11 pgs.

\* cited by examiner

LOW T

HIGH T

STRUCTURE, SYNTHESIS, AND APPLICATIONS FOR OLIGO PHENYLENE ETHYNYLENES (OPES)

CROSS-REFERENCE TO RELATED APPLICATIONS

This application is a U.S. National Stage Application under 35 U.S.C. 371 from International Application No. PCT/US2011/043908, filed Jul. 13, 2011 which claims benefit of U.S. Provisional Application Nos. 61/399,483, filed Jul. 13, 2010; 61/400,122, filed Jul. 22, 2010; 61/366,850, filed Jul. 22, 2010; 61/401,825, filed Aug. 19, 2010; 61/401,832, filed Aug. 19, 2010; 61/404,236, filed Sep. 29, 2010; 61/456,552, filed Nov. 8, 2010; 61/413,878, filed Nov. 15, 2010; 61/471,800 filed Apr. 5, 2011; and 61/499,097 filed Jun. 20, 2011; each of which is hereby incorporated by reference in its entirety.

STATEMENT REGARDING GOVERNMENT SPONSORED RESEARCH

This invention was made with Government support under grant number W911NF-07-0079 awarded by the Defense Threat Reduction Agency. The U.S. Government has certain rights in this invention.

BACKGROUND

Oligo phenylene ethynylenes (OPEs) are conjugated molecules that have a wide range of applications in electrically conducting materials, bio-chemical sensors, and supramolecular assemblies. More recently, interest has developed in the antimicrobial activity of these compounds. For example, while the extensive use of antibiotics has successfully dramatically reduced the human mortality rate due to infections, it has also given rise to the acquisition of resistance genes by various organisms, making some infections increasingly hard to treat. Accordingly novel methods for infection control, including novel methods and compounds for providing antimicrobial properties to a variety of materials is greatly desired.

SUMMARY

The present disclosure provides novel oligo phenylene ethynylene (OPE) compounds, methods for synthesizing these compounds, and materials incorporating these compounds.

According to an embodiment, the OPEs of the present disclosure have the base structure shown in FIG. 1 and where:
Where:
  n is selected from the group consisting of 1, 2, 3 and 4;
  A is selected from the group consisting of $C_2C_6H_2$ and $C_2C_4H_2S$;
  $B=C_2C_6H_2$,
  C=is either $C_6H_4$ or not present;
  X is selected from the group consisting of: $COOCH_2CH_3$, $O(CH_2)_kN(CH_3)_3^+$, $O(CH_2)_kSO_3^-$, and $O(CH_2)_k(C_6H_{12}N_2)C_6H_{13}^{2+}$;
  Y is selected from the group consisting of: $COOCH_2CH_3$, $O(CH_2)_kN(CH_3)_3^+$, $O(CH_2)_kSO_3^-$, $C_6H_2(OCH_3)_3$ and $O(CH_2)_k(C_6H_{12}N_2)C_6H_{13}^{2+}$;
where k is selected from the group of whole numbers from 1 to 10;
  $Z_A$ is selected from the group consisting of H and $O(CH_2)_j(C_6H_{12}N_2)C_6H_{13}^{2+}$; where j is selected from the group of whole numbers from 1 to 10;
  $Z_B$=H;
Wherein:
  if $Z_A$ is $O(CH_2)_j(C_6H_{12}N_2)C_6H_{13}^{2+}$, then $A=B=C_2C_6H_2$, $X=Y=COOCH_2CH_3$, and C is $C_6H_4$;
  if $Z_A$ is H, then:
    if A is $C_2C_6H_2$, $X=O(CH_2)_kN(CH_3)_3^+$, and $C=C_6H_4$, then $Y=O(CH_2)_kN(CH_3)_3^+$;
    if A is $C_2C_6H_2$ and $X=O(CH_2)_kN(CH_3)_3^+$, and C=is not present, then $Y=C_6H_2(OCH_3)_3$;
  if A is $C_2C_6H_2$ and $X=O(CH_2)_kSO_3^-$, then $C=C_6H_4$ and $Y=O(CH_2)_kSO_3^-$;
  if A is $C_2C_6H_2$ and $X=O(CH_2)_k(C_6H_{12}N_2)C_6H_{13}^{2+}$; then $C=C_6H_4$ and $Y=O(CH_2)_k(C_6H_{12}N_2)C_6H_{13}^{2+}$;
  if A is $C_2C_6H_2S$, then $C=C_6H_4$ and X is selected from the group consisting of $O(CH_2)_kN(CH_3)_3^+$ and $O(CH_2)_k(C_6H_{12}N_2)C_6H_{13}^{2+}$;
  wherein:
    if A is $C_2C_6H_2S$ and X is $O(CH_2)_kN(CH_3)_3^+$, then $Y=O(CH_2)_kN(CH_3)_3^+$;
    if A is $C_2C_6H_2S$ and X is $O(CH_2)_k(C_6H_{12}N_2)C_6H_{13}^{2+}$, then $Y=O(CH_2)_k(C_6H_{12}N_2)C_6H_{13}^{2+}$.

DETAILED DESCRIPTION

The present disclosure provides a plurality of novel compounds generally referred to herein as oligomeric phenylene ethynylenes (OPEs), methods of synthesizing OPEs and various uses for the OPEs. According to an embodiment, the present disclosure provides OPEs having the general structure shown in FIG. 1, where:

Where:

n is selected from the group consisting of 1, 2, 3 and 4;

A is selected from the group consisting of $C_2C_6H_2$ and $C_2C_4H_2S$;

B=$C_2C_6H_2$,

C=is either $C_6H_4$ or not present;

X is selected from the group consisting of: $COOCH_2CH_3$, $O(CH_2)_kN(CH_3)_3^+$, $O(CH_2)_kSO_3^-$, and $O(CH_2)_k(C_6H_{12}N_2)C_6H_{13}^{2+}$;

Y is selected from the group consisting of: $COOCH_2CH_3$, $O(CH_2)_kN(CH_3)_3^+$, $O(CH_2)_kSO_3^-$, $C_6H_2(OCH_3)_3$ and $O(CH_2)_k(C_6H_{12}N_2)C_6H_{13}^{2+}$;

where k is selected from the group of whole numbers from 1 to 10;

$Z_A$ is selected from the group consisting of H and $O(CH_2)_j(C_6H_{12}N_2)C_6H_{13}^{2+}$; where j is selected from the group of whole numbers from 1 to 10;

$Z_B$=H;

Wherein:

if $Z_A$ is $O(CH_2)_j(C_6H_{12}N_2)C_6H_{13}^{2+}$, then A=B=$C_2C_6H_2$, X=Y=$COOCH_2CH_3$, and C is $C_6H_4$;

if $Z_A$ is H, then:

if A is $C_2C_6H_2$, X=$O(CH_2)_kN(CH_3)_3^+$, and C=$C_6H_4$, then Y=$O(CH_2)_kN(CH_3)_3^+$;

if A is $C_2C_6H_2$ and X=$O(CH_2)_kN(CH_3)_3^+$, and C=is not present, then Y=$C_6H_2(OCH_3)_3$;

if A is $C_2C_6H_2$ and X=$O(CH_2)_kSO_3^-$, then C=$C_6H_4$ and Y=$O(CH_2)_kSO_3^-$;

if A is $C_2C_6H_2$ and X=$O(CH_2)_k(C_6H_{12}N_2)C_6H_{13}^{2+}$; then C=$C_6H_4$ and Y=$O(CH_2)_k(C_6H_{12}N_2)C_6H_{13}^{2+}$;

if A is $C_2C_6H_2S$, then C=$C_6H_4$ and X is selected from the group consisting of $O(CH_2)_kN(CH_3)_3^+$ and $O(CH_2)_k(C_6H_{12}N_2)C_6H_{13}^{2+}$;

wherein:

if A is $C_2C_6H_2S$ and X is $O(CH_2)_kN(CH_3)_3^+$, then Y=$O(CH_2)_kN(CH_3)_3^+$;

if A is $C_2C_6H_2S$ and X is $O(CH_2)_k(C_6H_{12}N_2)C_6H_{13}^{2+}$, then Y=$O(CH_2)_k(C_6H_{12}N_2)C_6H_{13}^{2+}$.

The OPEs disclosed herein can exist in solution, in colloidal suspensions, and attached, for example, by modification of the carboxyester "headgroup," to surfaces by various covalent linkages. All of the OPEs disclosed herein are fluorescent and demonstrate biocidal activity. Furthermore, some of the compounds have demonstrated viricidal and/or fungicidal activity as well.

Figure 1:
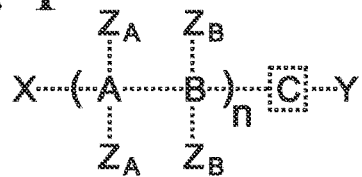
FIG. 1 depicts the basic structure of an OPE according to an embodiment of the present disclosure.
Figure 2:
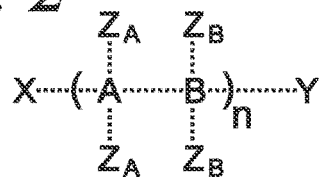
FIG. 2 depicts the basic structure of an OPE according to another embodiment of the present disclosure.

In general, the OPEs disclosed herein are formed from a single oxygen generator resonant structure core unit shown in FIG. 2 as (A and B) and a plurality of functional groups extending from the core unit. More specifically, the OPEs disclosed herein contain para-linked subunits of a conjugated aromatic oligomeric chain (A and B) with attached functional groups X and Y at the termini of the chain and functional groups $Z_A$, attached to the aromatic ring of subunit A and $Z_B$ attached to the aromatic ring of subunit B. Some of the OPEs disclosed herein may include a third resonant structure C, (shown in FIG. 1) which is an optional aromatic linking unit for functional group Y.

According to various embodiments, the specific OPEs of the present disclosure are obtained by various substitutes of the general structure shown in FIG. 1. Table 1 provides a list of the various substitutions that give rise to the OPEs of the present disclosure.

TABLE 1

FIG. 1 Substitutions

| A | B | C | X = | Y = | $Z_A =$ | $Z_B =$ | n = | j = | k = |
|---|---|---|-----|-----|---------|---------|-----|-----|-----|
| $C_2C_6H_2$ | $C_2C_6H_2$ | $C_6H_4$ | $COOCH_2CH_3$ | $COOCH_2CH_3$ | $O(CH_2)_j(C_6H_{12}N_2)C_6H_{13}^{2+}$ | H | 1, 2, 3 or | 1-10 | n/a |
| $C_2C_6H_2$ | $C_2C_6H_2$ | $C_6H_4$ | $O(CH_2)_{k1}N(CH_3)_3^+$ | $O(CH_2)_{k2}N(CH_3)$ | H | H | 1, 2, 3 or | n/a | 1-10 |
| $C_2C_6H_2$ | $C_2C_6H_2$ | $C_6H_4$ | $O(CH_2)_{k1}SO_3^-$ | $O(CH_2)_{k2}SO_3^-$ | H | H | 1, 2, 3 or | n/a | 1-10 |
| $C_2C_4H_2S$ | $C_2C_6H_2$ | $C_6H_4$ | $O(CH_2)_{k1}N(CH_3)_3^+$ | $O(CH_2)_{k2}N(CH_3)$ | H | H | 1, 2, 3 or | n/a | 1-10 |
| $C_2C_6H_2$ | $C_2C_6H_2$ | none | $O(CH_2)_{k1}N(CH_3)_3^+$ | $C_6H_2(OCH_3)_3$ | H | H | 1, 2, 3 or | n/a | 1-10 |
| $C_2C_6H_2$ | $C_2C_6H_2$ | $C_6H_4$ | $O(CH_2)_{k1}(C_6H_{12}N_2)C_6H_{13}^{2+}$ | $O(CH_2)_{k2}(C_6H_{12}$ | H | H | 1, 2, 3 or | n/a | 1-10 |
| $C_2C_4H_2S$ | $C_2C_6H_2$ | $C_6H_4$ | $O(CH_2)_{k1}(C_6H_{12}N_2)C_6H_{13}^{2+}$ | $O(CH_2)_{k2}(C_6H_{12}$ | H | H | 1, 2, 3 or | n/a | 1-10 |

In viewing the chart above, those of skill in the art will recognize that compounds can easily be formed to include various numbers of repeat units alkyl chain linkages to the quaternary ammonium bearing groups and/or the sulfonate bearing groups, as demonstrated, for example, by the k groups indicated above. Accordingly, while specific structures and methods of synthesis are disclosed below, it will be understood that similar structures bearing these repeat units are similarly contemplated by the present disclosure.

Figure 3:
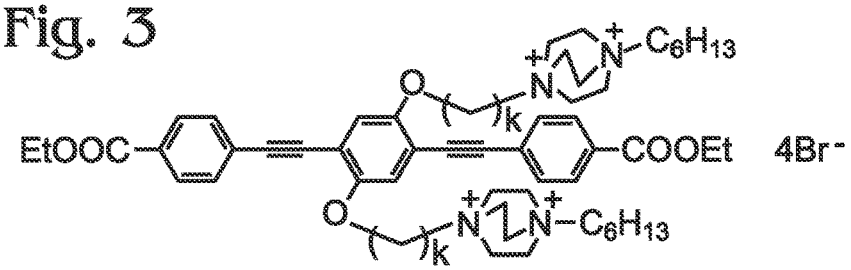
FIG. 3 is the chemical structure of OPE-1-DABCO.
Figure 10:
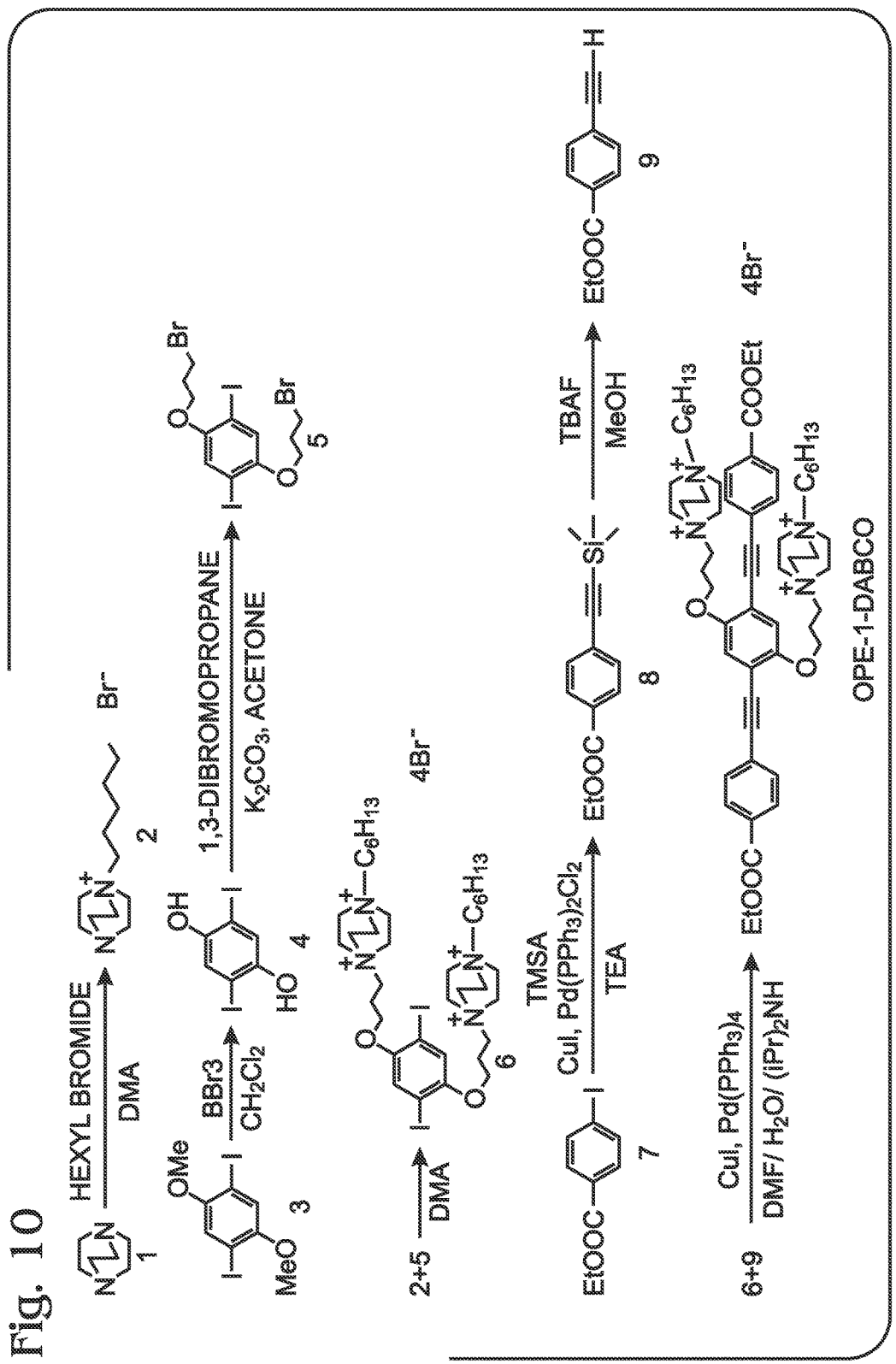
FIG. 10 is a schematic illustration of the synthesis scheme for OPE-1-DABCO.

FIG. 3 shows the chemical structure of OPE-1-DABCO. Suitable counterions for OPE-1-DABCO include Cl⁻, Br⁻ or I⁻. An exemplary synthesis scheme for OPE-1-DABCO where j is 3 is shown in FIG. 10. Synthesis for the scheme shown in FIG. 10 is as described below:

Compound 6. 1-Hexyl-4-aza-1-azoniabicyclo[2.2.2]octane Bromide (2) and 1,4-bis(3-bromopropoxy)-2,5-diiodobenzene (5) were prepared according to a literature procedure. 1,2 A solution of 0.35 g (1.25 mmol) of compound 1 and 0.3 g (0.5 mmol) of compound 5 in 5 mL of dimethyacetamide was stirred at 110° C. for 18 h. Upon cooling, 10 mL of cold ether was added to the reaction mixture. The resulting precipitates was collected by filtration and purified by hot filtration. White powder was recrystallized from water, yield 0.3 g (0.26 mmol).

Compound 9. 1.33 g (14 mmol) of trimethylsilylacetylene was added to a deoxygenated solution of 2.56 g (9.1 mmol) of compound 7, 102 mg (0.15 mmol) of Pd(PPh3)2Cl2, and 42 mg (0.22 mmol) of CuI in 30 mL of Et3N. The reaction solution was stirred at room temperature under argon overnight. The solvent was removed, and the solid was purified by flash chromatography on silica gel with hexane to yield a compound 8 (1.81 g, 81%). A solution of 0.81 g (3.29 mmol) of compound 8 in 20 mL of methanol was deoxygenated for 30 min and 1.0 M tetrabutylammonium fluoride solution in THF (9.95 mmol) was added to the flask under argon and the mixture was stirred at room temperature for 6 h. The solvent was removed and re-dissolved in methylene chloride and extracted with water twice. The combined organic solution was dried over MgSO4 and the solvent was removed at reduced pressure to yield a compound 9 (0.38 g, 66%).

OPE-1-DABCO. A solution of 0.1 g (0.087 mmol) of compound 6 and 0.033 g (0.191 mmol) of compound 9 in 4 mL of DMF/(iPr)2NH mixture was deoxygenated for 30 min. 4 mg (3 μmol) of Pd(PPh3)4, and 1 mg (5 μmol) of CuI were added and the resulting mixture was stirred at room temperature under argon for 18 h. The reaction solution was poured into 100 mL of acetone. The precipitated solid was collected by vacuum filtration and recrystallized from water, yield 0.09 g (85%).

Figure 4:
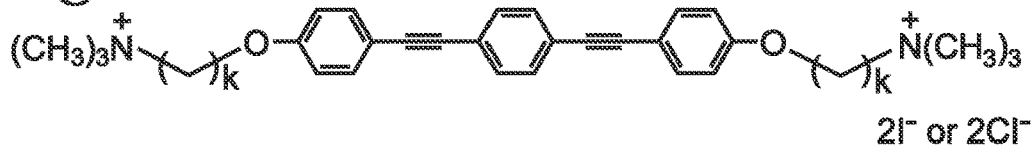
FIG. 4 is the chemical structure of EO-OPE-1 (A).
Figure 5:
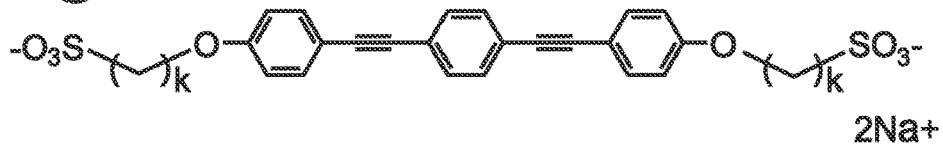
FIG. 5 is the chemical structure of EO-OPE-1 (S).
Figure 6:
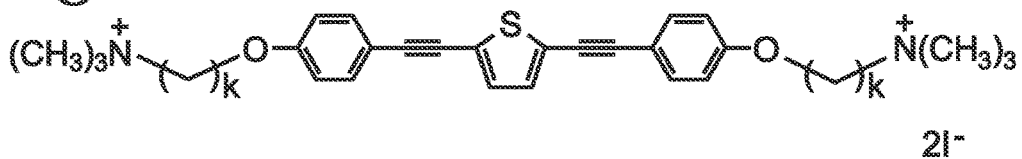
FIG. 6 is the chemical structure of EO-OPE-1 (Th, A).

FIG. 4 shows the chemical structure of EO-OPE-1 (A). Suitable counterions for EO-OPE-1 (A) include Cl⁻, Br⁻ or I⁻. FIG. 5 shows the chemical structure of EO-OPE-1 (S). Suitable counterions for EO-OPE-1 (S) include Na⁺ FIG. 6 shows the chemical structure of EO-OPE-1 (Th, A). Suitable counterions for EO-OPE-1 (Th, A) include Cl⁻, Br⁻ or I⁻. EO-OPE-1(A), and EO-OPE-1 (Th, A) each have two net positive charges and are quaternary ammonium salts without pendant groups attached to the middle aromatic ring. EO-OPE-1 (S) is anionic. As demonstrated below, these compounds kill Gram-negative bacteria such as *E. coli* and Gram-positive bacteria such as *Staphylococcus epidermis* (*S. epidermis*) and *S. aureus* under 365 nm radiation. Notably, EO-OPE-1 (Th, A) reaches 5 log killing against *S. aureus* with concentration as low as 5 ng/mL in a half hour irradiation.

Figure 11:
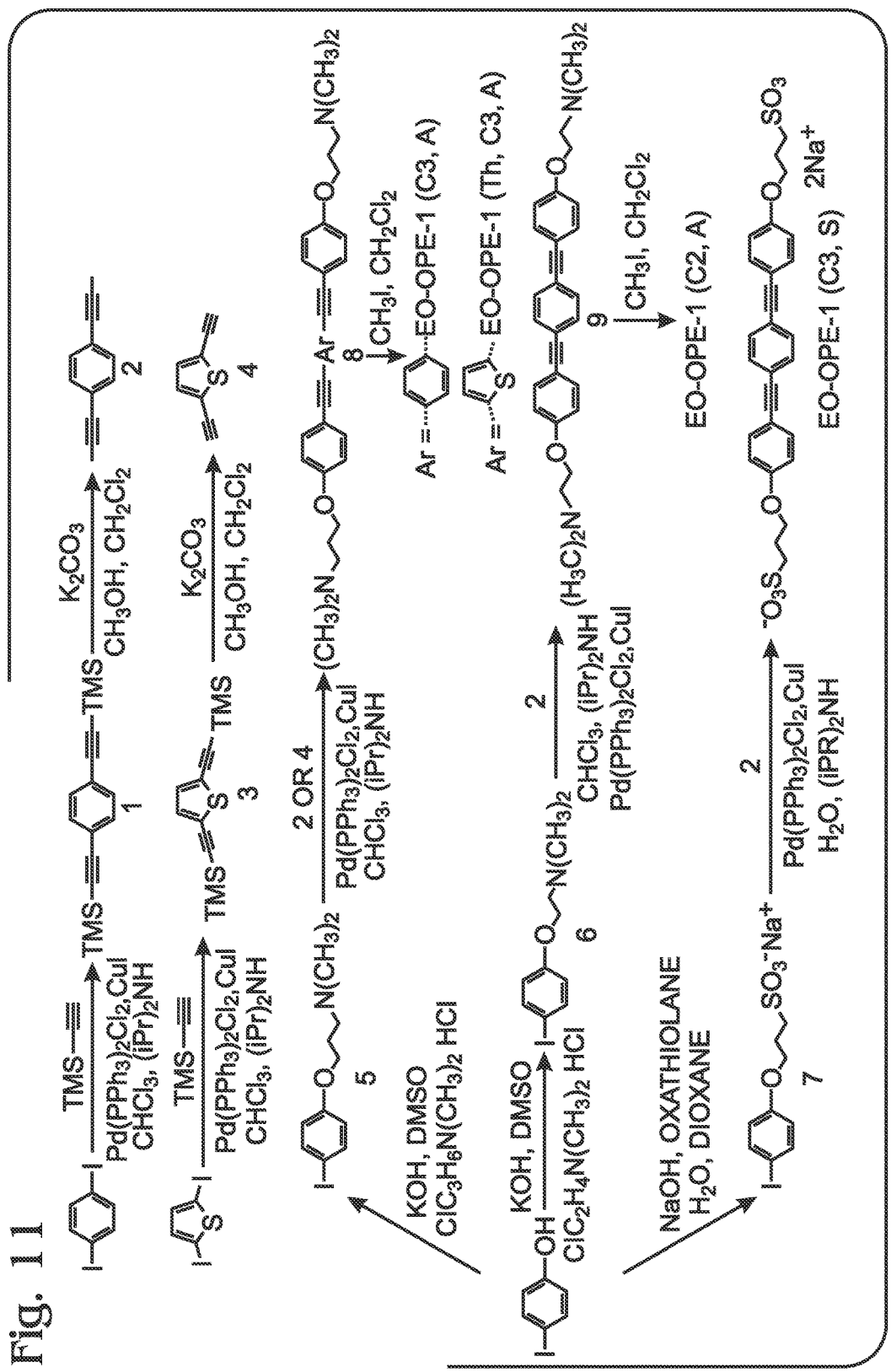
FIG. 11 is a schematic illustration of the synthesis scheme for EO-OPE-1 (A), EO-OPE-1 (C2, A), EO-OPE-1 (S), and EO-OPE-1 (Th, A).

An exemplary synthesis scheme for EO-OPE-1(C3, A) (wherein k=3), EO-OPE-1 (C2, A) (wherein k=2), EO-OPE-1 (C3, S) (where k=3) and EO-OPE-1 (Th, C3, A) (where k=3) is shown in FIG. 11. Briefly, each of these compounds as well as the synthetic intermediates were synthesized through multi-step reactions. 2,5-diiodothiophene, ethynyl(trimethyl)silane, 2,2-dioxide, 3-chloro-N,N-dimethyl-propan-1-amine, CuI, K2CO3, diisopropylamine, potassium biocarbonate, pd catalyst, 2-chloro-N,N-dimethyl-ethanamine, Oxathiolane, and 4-iodophenol, 1,4-diiodobenzene were purchased from Sigma-Aldrich (St. Louis, Mo.) and used as received. All of the solvents were HPLC grade purchased from Honeywell (Morristown, N.J.) and used without purification. The stains, Syto 9, Syto 24, and propidium iodide were obtained from Molecular Probes, Inc. (Eugene, Oreg.).

Synthesis of these molecules is straightforward, requiring five steps in each case. But yields (purification by chromatography) for the steps involving the conversion of compound 5 to 8, 5 to 9, and 6 to 10 are low. These results may be caused by poor solubility and high affinity to silica gel of 8, 10 and their intermediates such that the majority of products is absorbed on the silica gel. In addition, the instability of compound 4 may be responsible for the low yield of the conversion of 5 to 9. Target molecules are easily characterized by NMR (proton and carbon) and Mass Spectroscopy due to the relatively simple structures.

Turning to FIG. 11, the synthesis of EO-OPE-1(C3, A), EO-OPE-1 (C2, A), EO-OPE-1 (C3, S) and EO-OPE-1 (Th, C3, A) is shown and described below.

Compounds 1, 2, 3, and 4 were synthesized according to procedures described in Corbitt, et al., K.S. ACS Appl. Mater. Interfaces, 2009, 1(1), 48-52 and Lin et al., J. Phys. Chem. C, 2009, 113, 755-764, each of which is hereby incorporated by reference.

Synthesis of 5. A solution of 4-iodophenol (1 g, 4.54 mmol) in DMSO (5 mL) was prepared, then 3-chloro-N,N-dimethylpropylamine hydrochloride (2.73 g, 17.16 mmol) and crushed potassium hydroxide (2.5 g, 44.54 mmol) were added. The suspension was stirred at room temperature overnight. The resulting mixture was poured into 100 mL of H2O to give a precipitate. The solid was collected by filtration, and the solid was washed with H2O 3 times and dried in a vacuum desicator to give 1.24 g of white solid. Yield: 89%. 1H NMR (CDCl3, 500 MHz), δ 7.545 (d, 2H), δ 6.685 (d, 2H), δ 3.991 (t, 2H), δ 2.494 (t, 2H), δ 2.282 (d, 6H), δ 1.979 (m, 2H).

Synthesis of 8. 5 (1.53 g, 5.01 mmol), CHCl3 (21 mL), and diisopropylamine (2 mL) were mixed and degassed by purging argon gas for 30 min. 2 (383 mg, 3.0 mmol), Pd(PPh3)2Cl2 (92 mg, 0.131 mmol) and CuI (46 mg, 0.24 mmol) were added to the mixture which was stirred overnight. The salt formed in the process was removed by filtration, and the solution was extracted with dichloromethane and washed with NH4Cl solution, H2O, and saturated NaCl. The organic layer was dried over anhydrous MgSO4 for 30 min, and filtered to remove the MgSO4. The solvent was removed by vacuum rotary evaporation, and the residual solid was purified by column chromatography using a mixture of CH2Cl2 and CH3OH to give 520 mg of a white solid. Yield: 22%. 1H NMR (CDCl3, 500 MHz), δ 7.444 (m, 8H), 6.865 (d, 4H), 1H NMR (DMSO-d6, 500 MHz), δ 4.054 (t, 4H), δ 2.461 (t, 4H), δ 2.264 (s, 12H), δ 1.970 (m, 4H).

Synthesis of EO-OPE-1(C3, A). Compound 8 (25 mg, 0.052 mmol) and dichloromethane were mixed, then iodomethane (80 mg, 1.28 mmol) was added. The mixture was stirred at room temperature for 1 h, then the solid was collected by filtration, and washed with dichloromethane for 3 times. 39 mg of yellow solid was obtained after vacuum drying. Yield: 99%. 1H NMR (DMSO-d6, 500 MHz), δ 7.53 (m, 8H), δ 7.017 (d, 4H), δ 4.099 (t, 4H), δ 3.473 (t, 4H), δ 3.09 (s, 18H), δ 2.193 (m, 4H). $^{13}$C NMR δ 156.6, δ 131.1, δ 129.4, δ 120.5, δ 113.0, δ 112.5, δ 89.4, δ 85.8, δ 62.9, δ 60.9, δ 50.3, δ 20.5. MS (ESI). Calcd: m/z 510.3246. Obsd: m/z 510.3226.

Synthesis of 6. 4-iodo phenol (686 mg, 3.12 mmol), 2-chloro-N,N-dimethylethylamine hydrochloride (1.35 g, 9.35 mmol), potassium carbonate (2.34 mg, 17.16 mmol), and acetone (50 ml) were mixed together. The mixture was refluxed overnight. Acetone was removed under reduced pressure and the solid was dissolved in dichloromethane and washed with H2O twice, dried over MgSO4 for 30 min MgSO4 was removed by filtration and the solvent was removed under reduced pressure to give 863 mg of oil. Yield: 93%. 1H NMR (CDCl3, 500 MHz), δ 7.537 (d, 2H), δ 6.697 (d, 2H), 4.016 (t, 2H), δ 2.709 (t, 2H), δ 2.313 (s, 6H).

Synthesis of 10. Compound 6 (319 mg, 1.10 mmol), CHCl3 (16 mL) and diisopropylamine (0.6 mL) were mixed and degassed by purging argon gas for 30 min Followed the addition of 2 (46 mg, 0.37 mmol), Pd(PPh3)2Cl2 (10 mg) and CuI (6 mg) with stirring overnight. The salt formed in the process was removed by filtration, and the solution was extracted over dichloromethane and washed with NH4Cl solution, H2O and saturated NaCl. Organic layer was dried over anhydrous MgSO4 for 30 min, and filtrated to remove MgSO4. The solvent was removed by vacuum rotary evaporator, and resulted solid was purified by column chromatography to give 94 mg of white solid. Yield: 57%. 1H NMR (CDCl3, 500 MHz), δ 7.484 (m, 8H), δ 6.912 (d, 4H), δ 4.096 (t, 4H), δ 2.754 (t, 4H), δ 2.347 (s, 18H).

Synthesis of EO-OPE-1 (C2, A). Compound 10 (84.5 mg, 0.187 mmol) and dichloromethane were mixed, then iodomethane (265 mg, 1.87 mmol) was added. The mixture was stirred at room temperature for 1 h, then collected solid by filtration, and the solid was washed with dichloromethane for 3 times to give 126 mg of light yellow solid. Yield: 92%. 1H NMR (DMSO-d6, 500 MHz), δ 7.578 (m, 8H), δ 7.073 (d, 4H), δ 4.502 (t, 4H), 6 (t, 4H), δ 3.166 (s, 18H). 13C NMR δ 157.8, δ 133.2, δ 131.6, δ 122.4, δ 115.2, δ 91.3, δ 88.0, δ 64.0, δ 61.8, δ 53.1, δ 28.0. MS (ESI). Calcd: m/z 482.2933. Obsd: m/z 482.2908.

Synthesis of 9. Compound 5 (325 mg, 2.46 mmol) was dissolved in CHCl3 (15 mL) and diisopropylamine (1 mL) and degassed for 30 min Compound 4 (1.36 g, 4.46 mmol), Pd(PPh3)2Cl2 (56 mg, 0.08 mmol) and CuI (30 mg, 0.157 mmol) were added into the solution. The mixture was stirred at room temperature for 24 h followed by the Removal of solvent under reduced pressure. Further purification was achieved by column chromatography to give 25 mg of brown solid. Yield: 16%. 1H NMR (CDCl3, 500 MHz), δ 7.448 (d, 4H), δ 7.098 (d, 2H), δ 6.882 (d, 4H), δ 4.056 (t, 4H), δ 2.511 (t, 4H), δ 2.303 (s, 12H), δ 2.014 (m, 4H).

Synthesis of EO-OPE-1 (Th, C3, A). Dissolved compound 9 (54 mg, 0.11 mmol) in dichloromethane (2 mL) followed by the addition of iodomethane (70 mg, 0.47 mmol). Stirred at room temperature for 1 h and collected solid by filtration to give 85 mg of grey-brown powder. 1H NMR (DMSO-d6, 500 MHz), δ 7.532 (d, 4H), δ 7.339 (d, 2H), δ 7.017 (d, 4H), δ 4.112 (t, 4H), δ 3.488 (t, 4H), δ 3.091 (s, 18H), δ 2.184 (m, 4H). 13C NMR δ 159.1, δ 136.4, δ 133.2, δ 132.6, δ 123.5, δ 115.1, δ 94.2, δ 65.0, δ 62.9, δ 52.3, δ 22.5. Yield: 99%. MS (ESI). Calcd: m/z 516.2811. Obsd: m/z 516.2766.

Synthesis of 7. Under argon atmosphere, 4-iodophenol (0.5 g, 2.27 mmol) was rapidly dissolved in 2 mL of NaOH solution (10%) in an Erlenmeyer flask. A solution that contained Oxathiolane (0.35 g, 2.84 mmol) and 2 mL of dioxane was added to the above-mentioned solution at once. The resulting mixture was then stirred at room temperature for 4 h, and a quantitative precipitate formed. After cooling in an ice-water bath, the reaction mixture was filtered under reduced pressure. The obtained solid was washed with cold acetone and collected as white powder of 0.88 g. Yield: 99.9%.

Synthesis of EO-OPE-1 (C3, S). At room temperature, compound 7 (518 mg, 1.42 mmol) and compound 2 (100 mg, 0.79 mmol) were dissolved in a mixture of H2O (5 mL) and diisopropylamine (5 mL) under argon atmosphere. This reaction was kept under argon atmosphere at room temperature for 8 h. The reaction mixture was filtered under reduced pressure. 1H NMR (DMSO-d6, 500 MHz), δ 1.99 (t, 4H), 2.54 (m, 4H), 4.10 (t, 4H), 6.97 (d, 4H), 7.49-7.53 (m, 8H). 13C NMR δ 133.0, δ 131.4, δ 114.9, δ 79.3, δ 73.5, δ 66.9, δ 35.8, δ 30.8. MS (ESI). Calcd: m/z 553.0991. Obsd: m/z 553.0995.

In tests, EO-OPE-1(C3, A), and EO-OPE-1 (Th, C3, A) as well as other similar compounds PPE-DABCO, PPE-NMe3-Th, (described in co-pending patent application Ser. No. PCT/US2011/043922 filed Jul. 13, 2011, published as WO2012/009484 on 19 Jan. 2012) and OPE-n (described in co-pending U.S. patent application Ser. No. 13/001,478 and European Patent Application serial number 09771137.8) demonstrated significant antiviral activity, as shown in Example II, below.

Figure 7:
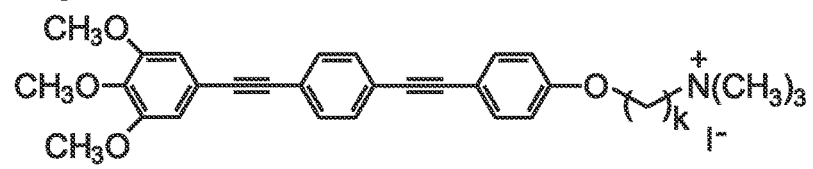
FIG. 7 is the chemical structure of TM.
Figure 12:
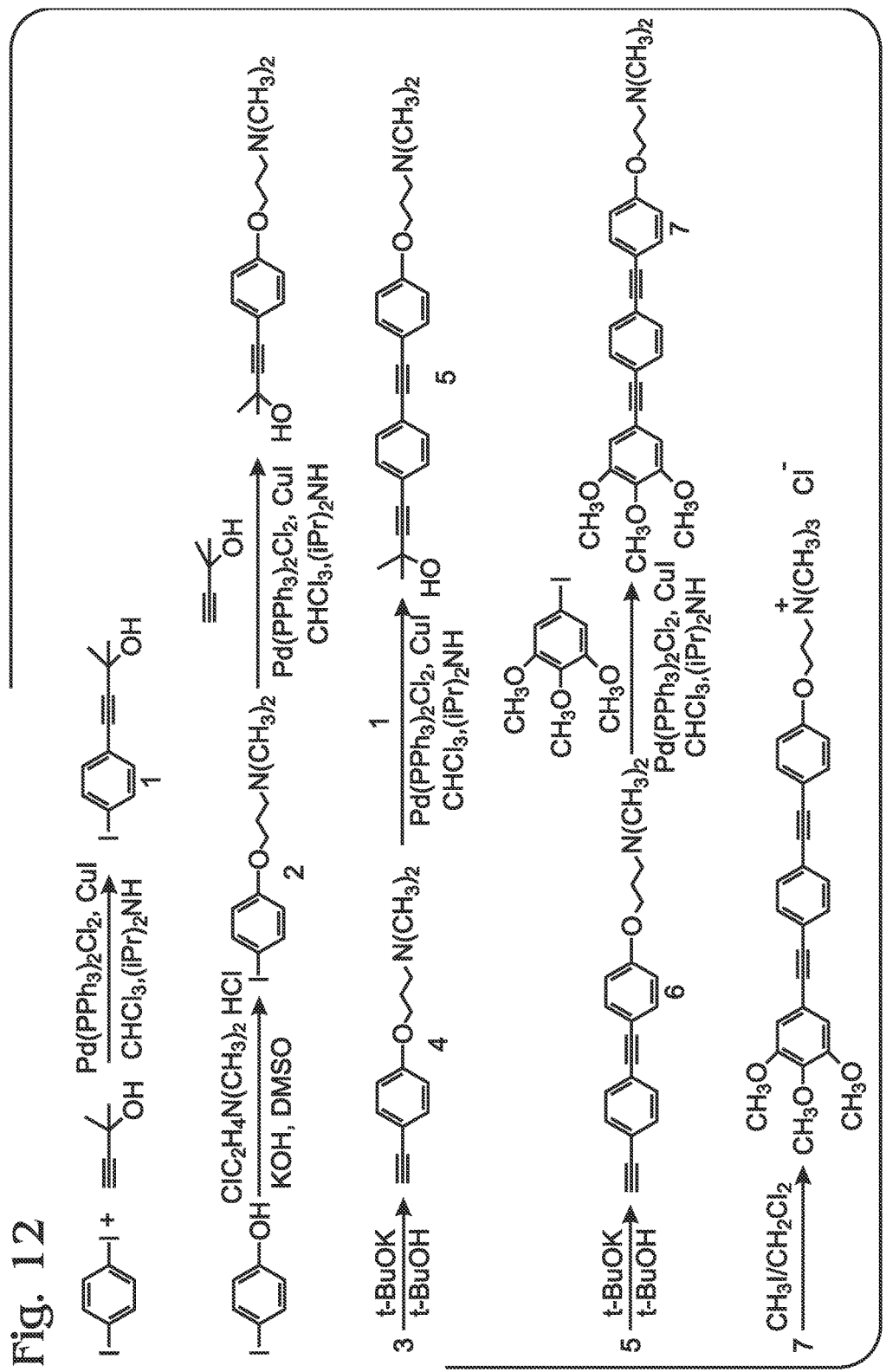
FIG. 12 is a schematic illustration of the synthesis scheme for TM.

FIG. 7 shows the chemical structure of TM. Suitable counterions for TM include Cl$^-$, Br$^-$ or I$^-$. An exemplary synthesis scheme for TM where k=3 is shown in FIG. 12. Synthesis according to the scheme shown in FIG. 12 is as follows:

Compound 2. At room temperature, 6.4 g (113.5 mmol) of KOH was suspended in 30 ml DMSO and then degassed for 10 min, followed by addition of 5 g (22.7 mmol) of 4-iodophenol, the solution was stirred for 5 min, finally 7.22 g (45.4 mmol) of ClC$_2$H$_4$N(CH$_3$)$_2$ HCl was added. The solution (suspension) was stirred at room temperature overnight (24 h). Then the suspension was added dropwise into 300 ml icy water with stirring to give white solid. The white solid was collected by filtration and washed with water for 4 times. The solid was dried over vacuum tank overnight. TLC:Hexane:DCM:CH3OH:TEA=4:1:1:0.2 (v/v). Yield: 97%

Compound 3. 11.9 g (39.25 mmol) of compound 2 was solubilized in 150 ml/20 ml CHCl3/Diisopropylamine then the solution was degassed for 20 min, then 550 mg (0.785 mmol) $Pd(PPh_3)_2Cl_2$ and 300 mg (1.57 mmol) CuI were added into this system and stirred for 5 min, followed by addition of 3.96/4.58 ml (47.1 mmol) 2-Methylbut-3-yn-2-ol. The solution was constantly stirred at room temperature for 25 hour at room temperature.

The resulting solution was resuspended in DCM and washed with NH4Cl solution, then water washed again. The organic layer was combined and dried over MgSO4 for over 15 min. Then MgSO4 was removed and the solvent was evaporated using evaporator. The residue was resolubilized in acetone and the solution was added into ice water dropwise to give solid. The solid was collected by filtration and dried over vacuum tank. TLC:Hexane:DCM:CH3OH:TEA=4:1:1:0.2 (v/v)

Compound 4. 5.17 g (19.8 mmol) of compound 3 was solubilized in 65 ml tert-BuOH at 45° C. The solution was degassed for 15 min, then 4.38 g (59.2 mmol) of tert-BuOK was added with one portion. The suspension was heated up to 82.5° C.

After 10 h reflux, the suspension was dripped into ice water to give fine yellow powder with stirring, and solid was collected by filtration. The solid was dried over vacuum tank. Yield: 100%

Compound 5. A solution of 50 ml CHCl3 7 ml DIPA was degassed for 15 min, followed by addition of 3.73 g (13 mmol) of compound 1, 171 mg (0.244 MMOL) of $Pd(PPH_3)_2 Cl_2$ and 93 mg (0.488 mmol) of CuI. The solution was stirred at room temperature for 5 min, and then compound 4 was added.

The solution was stirred at room temperature for 5 h. Then it was diluted by methylene dichloride, and washed with NH4Cl and water. The organic layer was dried over MgSO4 for 15 min. Then MgSO4 was removed by filtration and solvent was evaporated under vacuum. The residue was resuspended in cold acetone. White solid was collected by filtration and washed with cold acetone. Yield: 73%

Compound 6. Compound 5 was solubilized in 35 ml of tert-BuOH at 35° C. The solution was degassed for 15 min, then 0.45 g (4.04 mmol) tert-BuOK was added with one portion. The suspension was heated up to 82° C.

After 10 h reflux, the suspension was evaporated to remove tert-butanol and residue was washed with water and extracted with dichloromethane. If the reaction is not completed, purification may be undertaken by column chromatography. If the reaction is complete, standard deprotection, such as that described above, may be utilized.

Compound 7. 200 mg (0.659 mmol) of compound 6 is solubilized in 10 ml/2 ml (0.488 mmol) $Ch_2Cl_2$/diisopropyl amine and degassed for 15 min under Ar. Then, 10 mg/5 mg (0.01318/002636 mmol) $Pd(PPh_3)_2Cl_2$/CuI was added and degassed for 5 min followed by the addition of 290 mg (0.989 mmol) 5-Iodo-1,2,3-trimethyoxybenzene. The reaction is allowed to undertake overnight, and washed over saturated NH4Cl solution and extracted with dichloromethane twice. The organic lay is combined and dried over $MgSO_4$ for 30 min and $MgSO_4$ is removed by filtration and solvent was removed under reduced pressure. The residue is purified by column chromatography. Yield: 33%.

The standard procedure for methylation of OPE as described in Tang, Y et al. Langmuir 2009, 25, 21 was then followed. Yield: 100%

Figure 8:
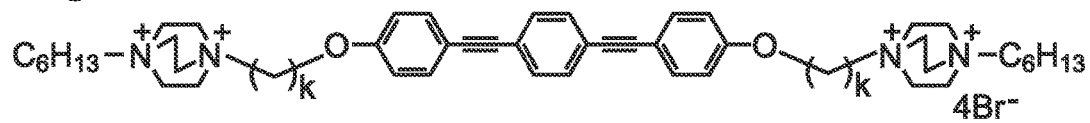
FIG. 8 is the chemical structure of EO-OPE-1-DABCO.
Figure 9:
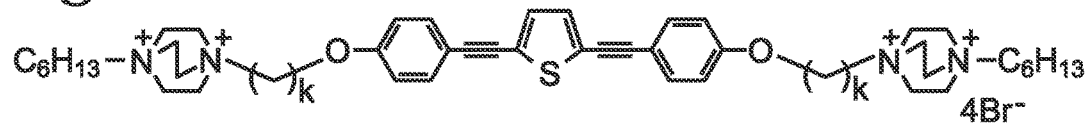
FIG. 9 is the chemical structure of EO-OPE1-Th-DABCO.
Figure 13:
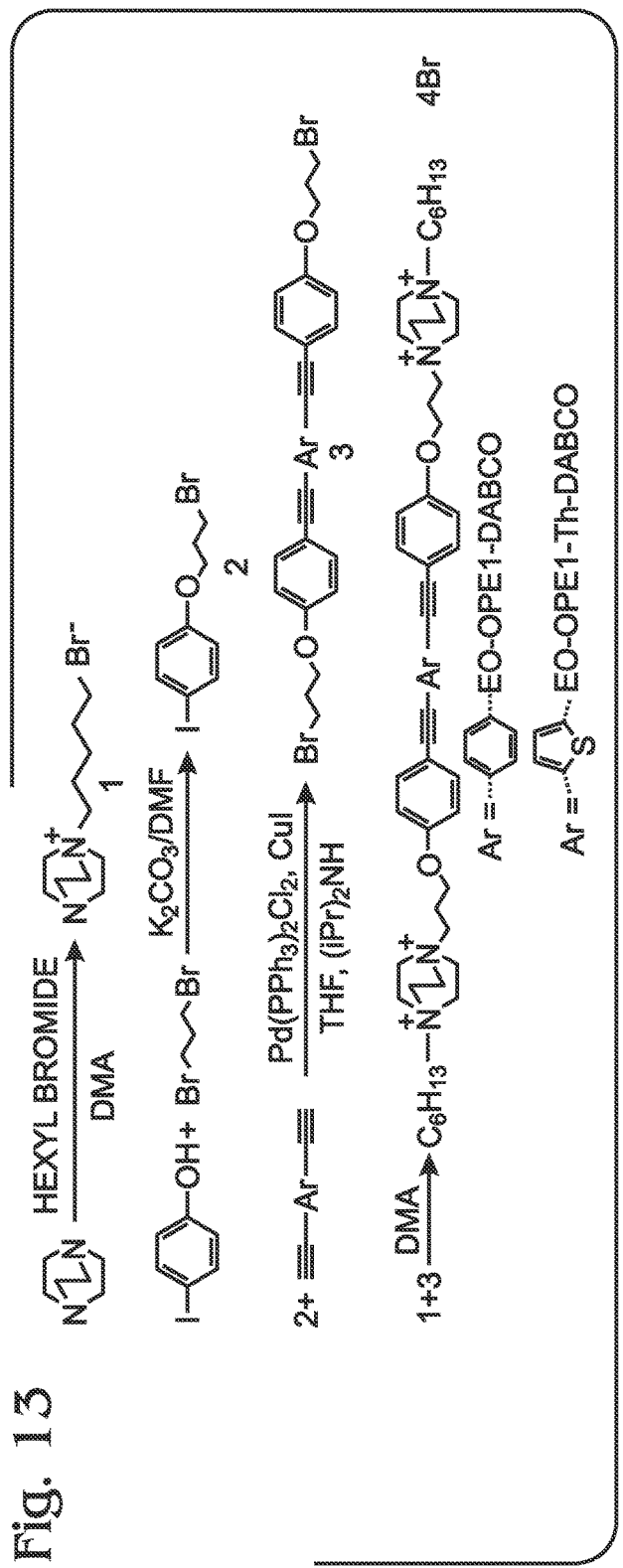
FIG. 13 is a schematic illustration of the synthesis scheme for EO-OPE-1-DABCO and EO-OPE1-Th-DABCO.

FIG. 8 shows the chemical structure of EO-OPE-1-DABCO. Suitable counterions for EO-OPE-1-DABCO include Cl⁻, Br⁻ or I⁻. FIG. 9 shows the chemical structure of EO-OPE1-Th-DABCO. Suitable counterions for EO-OPE1-Th-DABCO include Cl⁻, Br⁻ or I⁻. An exemplary synthesis scheme for EO-OPE-1-DABCO and EO-OPE1-Th-DABCO, where k=3 is shown in FIG. 13. Synthesis according to the scheme shown in FIG. 13 is as follows:

Compound 2. A solution of 4.4 g (20 mmol) of 4-iodophenol in 50 mL of DMF was slowly added to a solution of 8.1 g (40 mmol) of 1,3-dibromopropane and 11.1 g (80 mmol) of K2CO3 in 100 mL of DMF and the mixture solution was stirred at room temperature overnight. The resulting solution was mixed with methylene chloride and then washed with 10% KOH solution, water, and saturated NaCl solution. The organic solvent was removed and then recrystallized in hexane. The white solid was removed and hexane was removed from the filtrate. The remaining solution was kept in a refrigerator to obtain the solid. The resulting solid was washed with hexane, yield 2.5 g (37%).

Compound 4. 18 mg (15 μmol) of Pd(PPh3)2Cl2 and 4 mg (15 μmol) of CuI were added to a deoxygenated solution of 0.3 g (0.88 mmol) of compound 2 and 0.4 mmol of compound 3 in 10 mL of CHCl3/(iPr)2NH and stirred at room temperature under argon for 3 days. The solvent was removed and the solid was purified by flash chromatography on silica gel with CHCl3 to yield a compound 8.

EO-OPE1-DABCO and EO-OPE1-Th-DABCO. A solution of 253 μmol of compound 1 in 1 mL of DMA was added to a solution of 89 μmol of compound 4 in 2 mL of DMA and the mixture solution was stirred at 110° C. for 24 h. The resulting precipitates was collected by filtration and washed with CHCl3.

Each of the OPEs described herein has been tested for and has demonstrated significant dark and light-induced biocidal activity. An exemplary study is shown and described in Examples I and II, below. Accordingly, in yet another embodiment, the present disclosure provides novel biocides formed from or otherwise incorporating the OPEs described herein. Penetration of the bacterial membrane and binding of OPEs with DNA may provide paths for this activity. Further studies have shown that while OPEs are structurally diverse, they are generally amphiphilic due to the hydrophilic, charged side chains positioned along the rod-like hydrophobic PPE backbone. Dye leakage studies demonstrated a size dependent membrane perturbation against bacterial membrane mimics, with longer oligomers exhibiting higher activity than their smaller counterparts. Furthermore, the membrane perturbation activity appears to be selective with respect to specific types of membrane lipids that is, most OPEs perturbed bacterial but not mammalian membrane mimics, providing specificity that enables them to be used in a variety of environments, including those in which mammalian cells are present.

Furthermore, a number of the OPEs described herein (and all of those that were tested) demonstrated significant antiviral activity, as shown in Example III, below. Accordingly, in yet another embodiment, the present disclosure provides novel antivirals formed from or otherwise incorporating the OPEs described herein.

Moreover, as shown in Example IV, below, a Poly(Phenylene Ethynylene) PPE known as PPE-DABCO (disclosed in co-pending patent application Ser. No. PCT/US2012/043922, filed Jul. 13, 2011) has demonstrated significant antifungal activity. It is reasonable to assume that the OPEs disclosed herein that include DABCO (specifically OPE-1-DABCO, EO-OPE-1-DABCO, and EO-OPE1-Th-DABCO) would also have significant antifungal activity.

Accordingly, the OPEs disclosed herein are able to interfere with the pathogenicity a wide variety of pathogens, by inactivating, killing, or otherwise harming them. Thus, the OPEs described herein are suitable for attachment to, incorporation in, or association with a wide variety of substances and materials in order to prevent, reduce, or eliminate pathogens and pathogen-related harm caused to or by the substances and materials.

For example, the OPEs disclosed herein are suitable for attachment to or formation of fibrous or other materials in order to produce textiles or other (soft or hard) surfaces having antimicrobial, antiviral and/or antifungal properties. Thus, according to various embodiments, it may be desirable to have one or more of the OPEs disclosed herein functionally and robustly attached to a surface, for example via covalent linkages so that it can interfere with the pathogenicity of any pathogen the OPE comes into contact with. According to some embodiments, attachment of the OPE via chemisorption and physisorption may also be used.

Figure 14:
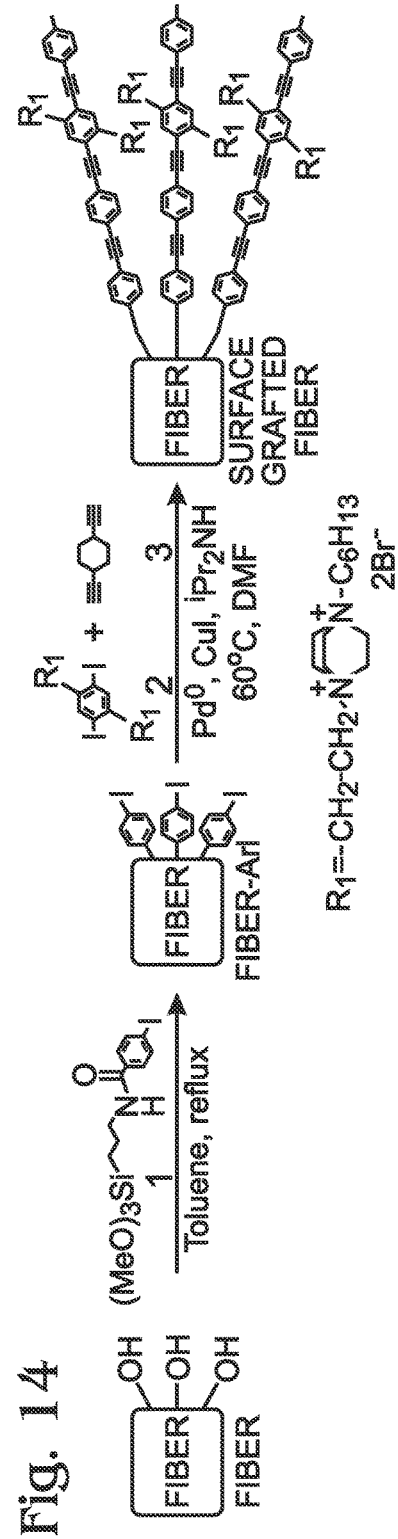
FIG. 14 shows an exemplary chemisorption scheme employing a step growth polymerization process.

In chemisorptions, a textile substrate is chemically activated with a primer or initiator and then reacted with a polymer or prepolymer to graft the conjugated polyelectrolyte to the surface in a step growth polymerization process. An exemplary chemisorption scheme employing a step growth polymerization process is shown in FIG. 14. Alternate reaction schemes may employ a living polymerization mechanism utilizing molecule by molecule propagation starting from a single molecule initiator.

In physisorption, the textile and conjugated polyeletrolyte are mixed under appropriate conditions such that the positively charged polymer attaches to the negatively charged textile surface. Typically the OPE is dissolved in a solvent (e.g., water or methanol) and the fabric is "dyed" with the solution.

Alternatively, according to still an embodiment, an initial organosilane attachment may be used as a synthetic approach to accomplish surface grafting. See, e.g., Ogawa, K.; Chemburu, S.; Lopez, G. P.; Whitten, D. G.; Schanze, K. S. "Conjugated Polyelectrolyte-Grafted Silica Microspheres" Langmuir, 2007, 23, 4541-4548, which is hereby incorporated by reference. By putting an organic iodine on the substrate we have grafted OPEs on nano- and microparticles and planar surfaces. This silane approach may also be used to graft OPEs onto fabrics. Furthermore, this approach can be easily extended to provide more robust linkages than silanes, using modified chemistries for attaching OPEs to surfaces including ester, ether and amide linkages as needed.

Accordingly, the OPEs described herein may be incorporated into or onto hard or soft surfaces using the techniques described above or, alternatively, by other known casting, electrospinning, dipping, or coating techniques. However, it is noted that the photophysical properties of OPEs are dependent on planarity which can be affected by self-assembly onto a substrate or placement in a poor solvent. Accordingly, these factors should be considered and taken into account when selecting a particular attachment or incorporation method.

As a still further embodiment, the OPEs may themselves be formed into fibers, for example via electrospinning.

It will be appreciated that any suitable fabric or material, including natural and/or synthetic fibers and materials may be used as an attachment surface for the OPEs described herein. According to some embodiments, suitable fabrics may comprise or consist of natural fibers such as cotton, silk and/or wool, or suitable blends thereof. Blended fabrics may include only natural fibers, only synthetic fibers, or both natural and synthetic fibers. In some cases, the antimicrobial polymers described herein may be incorporated into electrospun fibers for woven fabrics including, but not limited to filters. Other suitable textiles may include, but are not necessarily limited to rayon, nylon, or blends of cotton, silk, wool or other natural fabrics or fibers with synthetic fabrics or fibers of rayon or nylon.

Potential uses of fibers may include prophylaxes for potentially contaminated surfaces including mattresses and bed linens, countertop coverings, tablecloths, curtains and various swabs, bandages, sterile mats and liners for use both inside and outside a sterile/clinical environment or in food-preparation areas. Their uses may be directed against known contamination, as in a wound infection, or applied as a deterrent to propagation of pathogenic agents in such applications as coverings for common fomites. Treatments of the compounds onto various cellulosic components would also enable their use as filter elements for water purification.

Different blends to specifically release or retain killed bacteria could be developed based on combination of polymers with the desired retention properties. This could be effected either by use of varied polymer proportions in a single layer coating or by building multiple layers with the required external affinities.

According to some embodiments, the OPEs described herein may be incorporated into materials having commercial, industrial and/or household applications. Alternatively, the OPEs described herein may be used as or incorporated into antimicrobial, antivirial or antifungal coatings for such materials. For the purposes of this application, it should be noted that the term "material" incorporates both "soft" and "hard" substances including organic and inorganic matter such as, but not limited to, natural and man-made fabrics, plant-based materials, metals, polymers, wood, stone, plastic, and the like.

Examples of suitable medical applications for the OPEs described herein include bedsheets, hospital garments, curtains, floor and wall materials, air filtration systems, medical devices, bandages, surgical instruments, gloves, masks, lab coats, gauze orthopedic prostheses, bedding, bed frames, mattress covers, surgical furniture, dividers, curtains, carts for transport of medication, linens, dental trays, incise drapes, wound dressings, and implants.

Applications for the building industry include the coating or incorporation of OPEs in wall laminates, hand rails, pulls, trims, door handles, slings, hoists, window blinds, paints, sealants, polishes, and plastics.

Other applications include coatings for keyboards, gaming devices, toys, (for example, but limited to, in a daycare environment), industrial, commercial and household kitchens, food preparation equipment and utensils or any other surface where a sterile environment is desirable.

According to various embodiments, the OPEs described herein may be incorporated into various aspects of filtrations devices. For example, the antimicrobial polymers may be incorporated into filter elements for air filtration systems such as those used in commercial or residential buildings, cars, buses, trains airplane cabins etc. Alternatively or additionally, the antimicrobial polymers may be incorporated into commercial or household water or other liquid filtration systems by application of coatings on equipment and incorporation into and/or coating on filters. Alternatively or additionally, the antimicrobial polymers described herein may be utilized in recoverable bacterial absorbents (by filtration or magnetic components) in the form of coated beads or other suitable substrates. Furthermore, they may be incorporated in separation membranes for bacterial exclusion, extraction, and/or immobilization. They may also be incorporated into or used as a coating for disposal bags for biological waste or other (potentially) contaminated materials.

Other applications include in-can or in-tank preservation of aqueous functional fluids. This may include incorporation of the presently described OPEs into polymer emulsions, paints and coatings, adhesives and sealants, mineral slurries, metal working fluids, cosmetics and personal care products and cooling and recreational water. (See, e.g., Bruns et al. "Directory of Microbiocides for the protection of materials: A Handbook Chapter 3 R&D in material protection: new biocides," Wilfried Paulus, Ed.; Springer (2005).

Specific combinations and directed multilayer constructs may lend themselves to either single use or multiple uses, depending on the sequestration properties of that given combination. For example, coatings that have a high affinity for microbial binding may lend themselves more to single use applications (i.e. bandages or wipes) and those that would release microbial material, either upon washing or other decontamination could undergo multiple uses (i.e. bed linens, tablecloths).

According to various embodiments, the OPEs disclosed herein may be used to form or otherwise incorporated into gels or other materials. These gels or other materials may further include other biologically active materials. Much recent work has been devoted to the development of materials whose properties can be altered drastically by relatively small changes in properties such as temperature, pressure, solution or suspension properties (including but not limited to pH); these "stimuli responsive materials" (SRM) are often prepared as polymers or as surfaces prepared from components that can be covalently linked or self-assembled on surfaces. Smart polymers that have found use in biotechnology and medicine have been described by I Yu Galaev in Russian Chemical Reviews 64: 471-489 (1995); A. S. Hoffman in Clinical Chemistry 46:1478-1486 (2000) and H. G. Schild, Prog. Polym. Sci. 17, 163 (1992), incorporated herein by reference.

Prominent examples of SRMs include poly(N-isopropylacrylamide) (PNIPAAM) and oligo-ethylene glycol oligomers terminated with a thiol (OEG). The former can be grown from a surface by attaching an initiator monomer to a surface and following this with in situ polymerization. Through an ATRP process; the thickness of the resulting film can be controlled as a function of incubation time at a fixed catalyst and monomer concentration. The OEGs can be attached to a surface (usually Au) by covalent assembly as a self-assembled monolayer (SAM). For surfaces coated with either PNIPAAM or OEG there is a strong temperature dependence of the film properties. In both cases, films formed from these materials in contact with an aqueous solution exist as hydrated, expanded films at low temperatures that are relatively unreactive and non-adsorbtive towards various biological species including proteins, cells, bacteria, viruses, and the like. Above a specific lower critical solution temperature (LCST) the films contract, releasing water and become very hydrophobic. At temperatures higher than the LCST films from either SRM become thinner and strongly attract proteins, cells and other biological species that do not bind below the LCST.

According to yet another embodiment, the present disclosure provides films and assemblies containing both SRM components and the PPEs described herein. In general, these assembles provide a novel functional material that can be switched between active and inactive forms wherein, in the active form, the material is able to capture a biological species of interest and, in the inactive form, the material is able to release the biological species. In some embodiments the material can be switched between active and inactive forms repeatedly, allowing for reuse of the same material. Films containing these two functional components can be readily prepared by covalent synthesis or by a self assembly process employing a mixture of individual SRM and OPE thiols.

Figure 15:
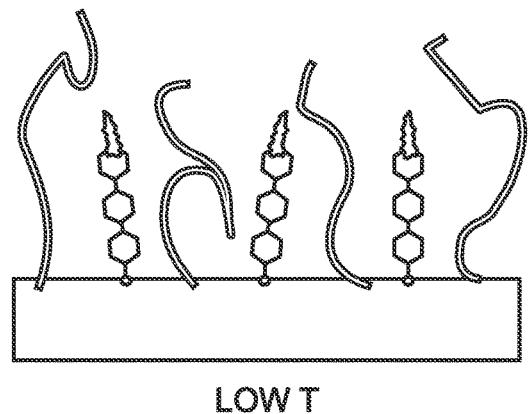
FIG. 15 shows an OPE hidden amidst the expanded form of an SRM.
Figure 16:
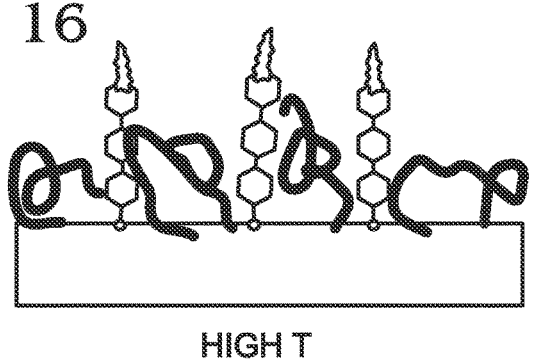
FIG. 16 shows an OPE unsheathed after exposure to a higher temperature.

Viewing FIG. 15 it can be seen that at low temperatures an OPE of appropriate length is buried amidst the expanded form of the SRM and inaccessible to any biological species (such as a protein, cell, bacteria, virus, etc.) present in the aqueous media. Moreover, these species are not attracted to the surface and do not associate with it. However, as the temperature is elevated above the LCST, contraction of the SRM component "unsheathes" the OPE, as shown in FIG. 16. Both components are now hydrophobic and strongly attractive. Accordingly, the unsheathed OPE is able to form a complex with the biological species.

Accordingly, in one embodiment, the presently described structure can form a reusable biocidal material. Under low temperatures the antimicrobial activity of the OPE is masked by the extended SRMs and therefore inactive. As stated above, elevation of the temperature above the LCST unsheathes the OPE, which is then allowed to form a complex with, thereby trapping, the bacteria. The OPE's biocidal activity is then exploited to inactivate, kill or destroy the trapped species, under either dark conditions or under uv light irradiation. Following destruction of the pathogen, the film will typically be contaminated with debris from the killed bacteria or cell. Returning the film to temperatures lower than the LCST results in expansion of the SRM, forcing the debris away from the OPEs. The result is a self-cleaning, reusable, biocidal film.

Examples of other practical uses for these mixed films include employing them as an active sensor which can be monitored by steady state fluorescence or by laser interferometry. The attachment of protein, cells or bacteria to the surface can be detected, for example, by the monitoring irradiation.

Figure 17:
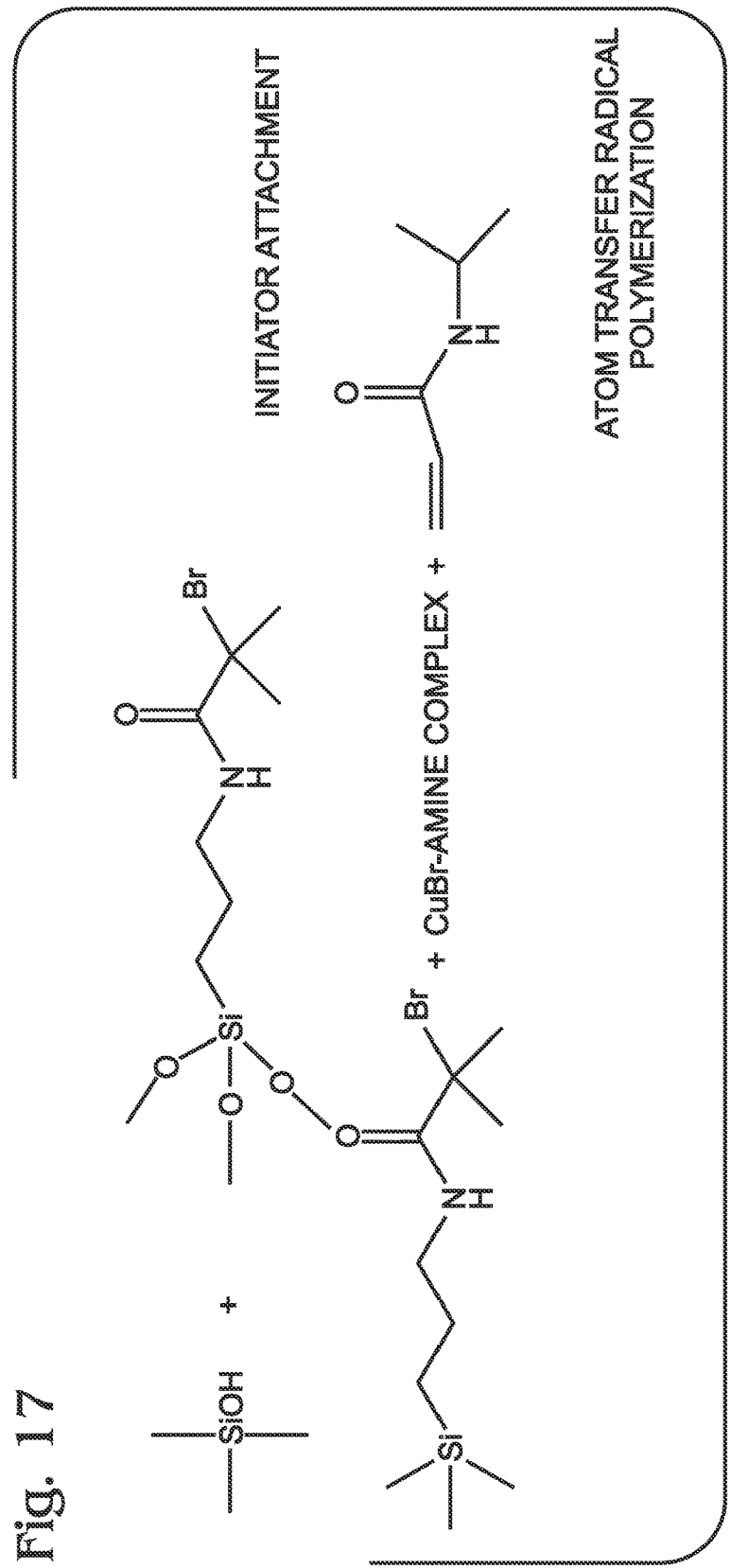
FIG. 17 depicts a method of synthesis of PNIPAAM by monomer polymerization onto an initiator functionalized surface.
Figure 18:
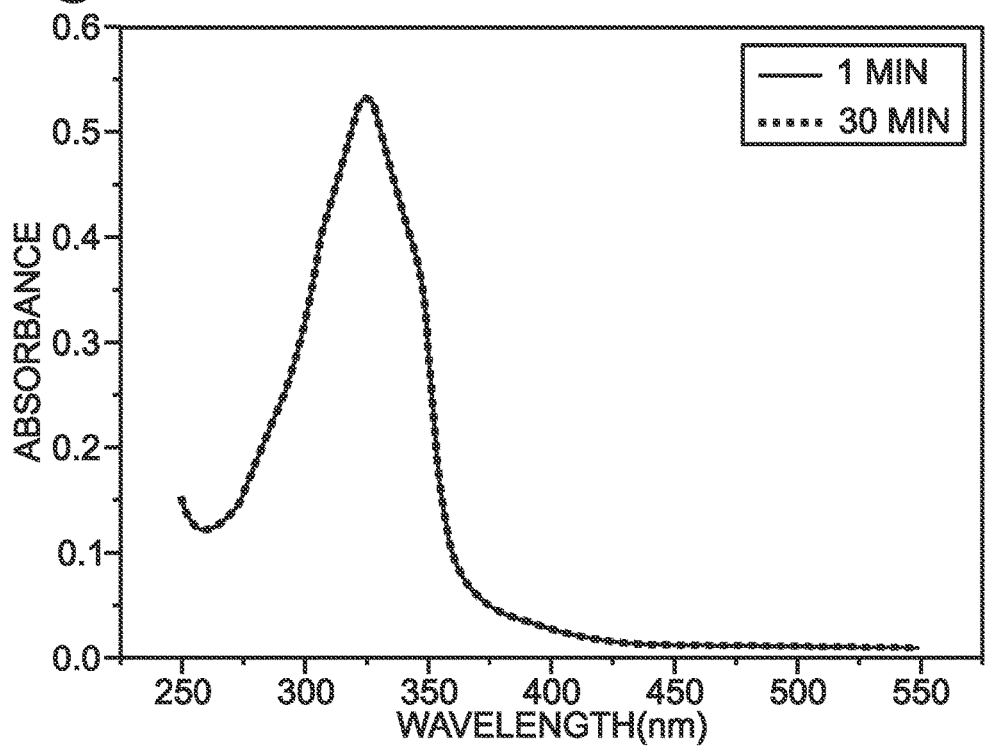
FIG. 18 shows the absorbance of EO-OPE-1 (C2, A).
Figure 19:
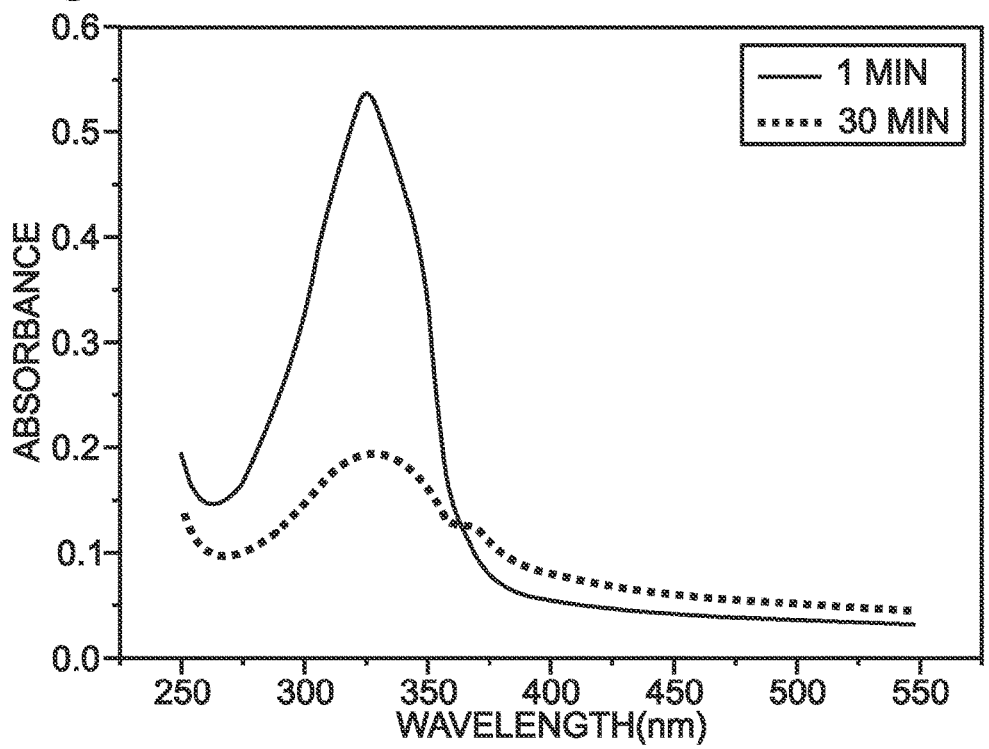
FIG. 19 shows the absorbance of EO-OPE-1 (C3, A)
Figure 20:
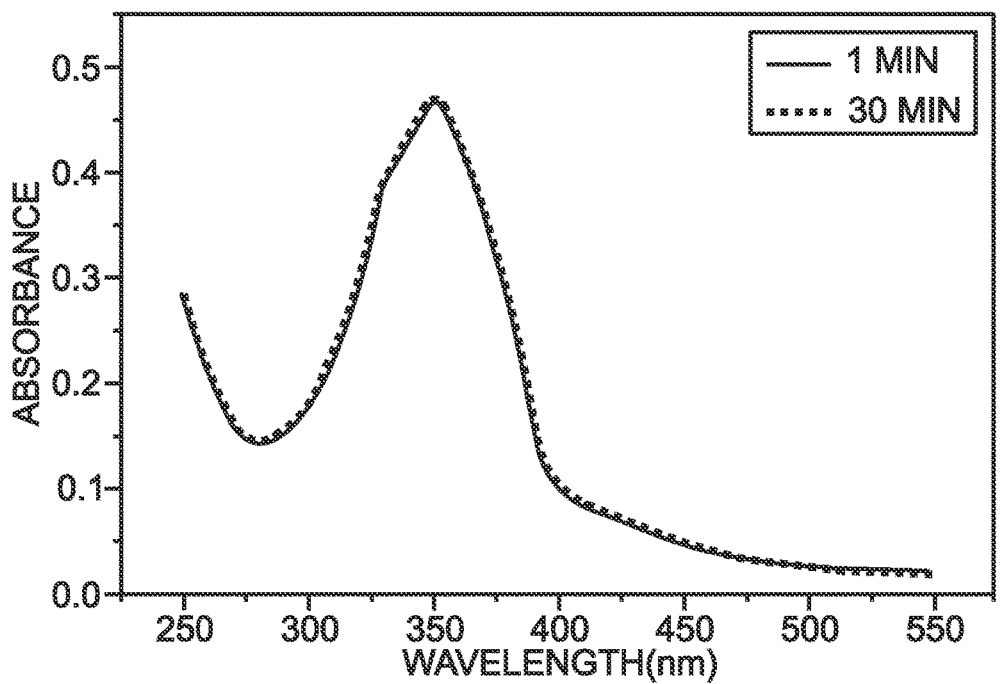
FIG. 20 shows the absorbance of EO-OPE-1 (Th, C3, A).
Figure 21:
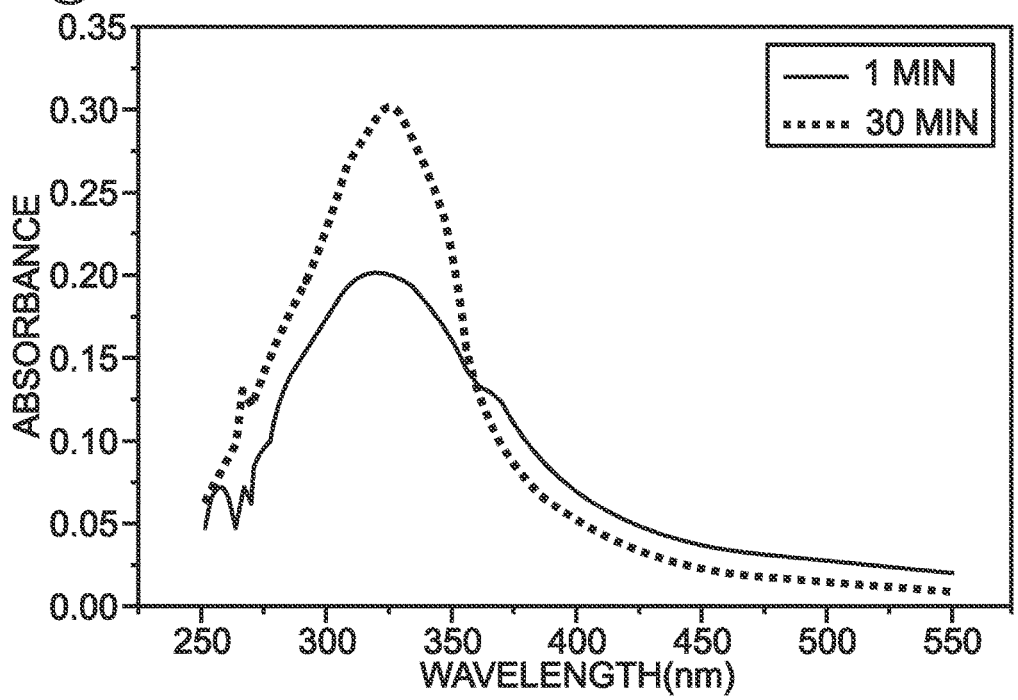
FIG. 21 shows the absorbance of EO-OPE-1 (C3, S).

The present disclosure further provides methods of manufacturing the functional materials described herein. Thiol terminated OEG derivatives are commercially available in a wide range of structures. A method of synthesis of PNIPAAM by monomer polymerization onto an initiator functionalized surface is shown in FIG. 17.

As stated above, at least some of the compounds described herein are useful in sensing applications. One particularly useful sensing application is DNA detection. Accordingly, the present disclosure provides a novel DNA detection mechanism. According to various embodiments, this detection mechanism does not involving labeling of the DNA and furthermore, is able to differentiate between single and double stranded DNA. Specifically, some OPEs display circular dichroism (CD) signals when bound to either single stranded (ss) or double stranded (ds) DNA. Moreover, in some cases, the signals are noticeably different depending on whether the OPE is bound to ds or ss DNA. Accordingly, this signal differential can be exploited to detect hybridization events.

Similarly, some OPEs display detectable fluorescence when bound to ds or ss DNA. Again, some compounds reflect a noticeable difference in the fluorescence spectra when bound to ds versus ss DNA.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

As used herein and in the appended claims, the singular forms "a," "an," and "the" include plural reference unless the context clearly dictates otherwise.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

EXAMPLES

Example I—Biocidal Activity of EO-OPE-1(C3, A), EO-OPE-1 (C2, A), EO-OPE-1 (C3, S) and EO-OPE-1 (Th, C3, A)

Dead/live assays were performed to test the biocidal activity of EO-OPE-1(C3, A), EO-OPE-1 (C2, A), EO-OPE-1 (C3, S) and EO-OPE-1 (Th, C3, A) against *E.coli, S.epidermis*, and *S.aureus*. *E.coli, S.epidermis*, and *S.aureus* were cultured in 50 mL of Difco™ Nutrient broth (LOT 4057492, Becton, Dickinson and Company, Sparks, Md. 21152 USA), Difco™ Nutrient broth (LOT 4057492, Becton, Dickinson and Company, Sparks, Md. 21152 USA), and BBL™ Brain Heart Infusion (LOT 8263271, Becton, Dickinson and Company, Sparks, Md. 21152 USA), respectively, for 18 h at 37° C. under shaking. The bacteria were collected by centrifuging 50 mL of culture at 4,000 rpm in an Eppendorf centrifuge for 15 min at 4° C. The pellet was re-suspended with the assistance of vortex in 25 mL of 0.85% NaCl solution and repelleted. The wash cycle was repeated twice. Bacterial concentrations were measured and normalized using a disposal hemocytometer (INCYTO Co., Ltd), counts being 2.5~3.0×107/mL. The diluted bacteria suspension was added to 1.5 mL of black and transparent microtubes in aliquots of 500 µL for dark and light samples, respectively. Three groups of live controls were prepared with cells suspended in black microtubes, transparent microtubes, and quartz cuvettes at the same concentrations, but without chemicals. These bacteria samples were titrated by OPEs with various concentrations followed by staying in dark for dark samples/controls and exposing to UV irradiation in a photoreactor chamber for light samples/controls with certain duration.

Dead/live assays were carried out using two sets of stains: SYTO 9/Propidium iodide for *E.coli* and SYTO 24/Propidium iodide for *S.epidermis* and *S.aureus*. SYTO 9 and SYTO 24 are cell membrane permeant nucleic acid stains with green (~498 nm for SYTO 9 and ~515 nm for SYTO 24) fluorescence and used to stain both live and dead cells; Propidium iodide is a red-fluorescent nucleic acid stain that is membrane impermeable to viable cells but stains DNA or RNA of dead cells with comprised membranes and emits red (~617 nm) fluorescence, indicating cell death. Upon the completion of the above treatment, a 1 to 1 ratio mixture of the two dyes was prepared and added into the samples (2.4 µL mixed dyes for 500 µL suspension) and incubated for 15 minutes in the dark. Bacteria were then examined under a 40× oil objective on a Zeiss LSM 510 Meta confocal laser scanning microscope and an Accuri C6 flow cytometer to identify and quantify those live and dead bacteria.

Photophysical study. For the absorption and fluorescence spectroscopy, we prepared a stock solution with concentration of 1 mM oligomer and 10% v/v solution of DMSO in H2O. 30 µL of the sonicated suspension of each EO-OPE-1 was diluted into 3 mL solution in a quartz cuvette to give a concentration of 10 µM. Absorption and fluorescence were performed on plate reader (SpectroMax M-5 microplate reader, Molecular Devices) at 24° C. Transient absorption spectra were recorded for EO-OPE-1 samples in both methanol and water. Transient absorption spectra were collected using laser systems that are described elsewhere 1, 2. The optical density was adjusted to 0.7 at the excitation wavelength (355 nm) with the laser energy being 6-7 mJ. Solutions were purged with argon for 45 mM before making transient absorption spectroscopy measurements.

Results and Discussion

Absorption and fluorescence. Given that there are only two hydrophilic groups attached on both ends of EO-OPE-1(C3, A), EO-OPE-1 (C2, A), EO-OPE-1 (C3, S) and EO-OPE-1 (Th, C3, A) through a large hydrophobic aromatic segment, these compounds are poorly soluble in water, moderately soluble in CH3OH, but quite soluble in DMF and DMSO. Further photophysical studies indicate that absorbance intensity at 1 mM for EO-OPE-1 (C2, A) and EO-OPE-1 (Th, C3, A) under the concentration at 10 µM in H2O is the same as that measured at 30 mM later, in contrast, the intensity of EO-OPE-1(C3, A) is enhanced around 2 times over 30 min and EO-OPE-1 (C3, S) is enhanced 1.5 times than that measured at 1 mM (See FIGS. 18-21). This indicates that EO-OPE-1(C3, A) and EO-OPE-1 (C3, S) dissolve in water more slowly than the other OPE. Basically, this series of biocides have been demonstrated to be very efficient light harvesters with large molar extinction coefficients in water (See Table II, below).

TABLE II

|  | EO-OPE-1 (C3, S) | EO-OPE-1 (C3, A) | EO-OPE-1 (C2, A) | EO-OPE-1 (Th, C3, A) |
|---|---|---|---|---|
| Molar extinction coefficient(ε)§ | $2.23 \times 10^4$ | $5.58 \times 10^4$ | $5.32 \times 10^4$ | $4.77 \times 10^4$ |
| Fluorescence quantum yields(Φf)* | $0.50 \pm 0.07$ | $0.52 \pm 0.05$ | $0.59 \pm 0.05$ | $0.46 \pm 0.02$ |
| τ3/μs in H2O | 5.2 | 17.9 μs | 18.7 μs | 7.2 μs |
| τ3/intensity in H2O | 0.06 | 0.07 | 0.065 | 0.15 |
| τ3/λmax(nm) in H2O | 543 | 545 | 541 | 510 |

EO-OPE-1(C3, A), EO-OPE-1 (C2, A), EO-OPE-1 (C3, S) and EO-OPE-1 (Th, C3, A) also have excellent fluorescent quantum yields (Qf) in water being 0.59, 0.52, 0.46, and 0.50 respectively.

Singlet oxygen generation. Excited triplet state (ETS) plays an essential role in the generation of ROS and 1O2. For triplet state study, in general, the lower intensity of transient absorption (TA) was observed in water than in methanol (lower triplet yield in water in comparison to methanol). Another important point to note is that all members of EO-OPE-1 series underwent fast photobleaching in water during TA experiments (approximately 40-50% reduction in signal intensity). To minimize the error due to photobleaching, fresh samples were prepared and used in each run. The results show that EO-OPE-1 (Th, C3, A) obtains the highest TA intensity, however, EO-OPE-1 (C2, A), EO-OPE-1(C3, A), and EO-OPE-1 (C3, S) are comparable. On the other hand, the triplet lifetimes for EO-OPE-1(C3, A), EO-OPE-1 (C2, A), EO-OPE-1 (C3, S), and EO-OPE-1 (Th, C3, A) are 5.2 μs, 17.9 μs, 18.7 μs, and 7.2 μs, respectively. Based on the above discussions, we would expect C will give a higher yield of 1O2, with lower yields for EO-OPE-1 (C2, A), EO-OPE-1(C3, A), and EO-OPE-1 (C3, S).

Biocidal study. The biocidal activities of the EO-OPE-1s containing cationic quaternary ammonium groups when exposed to 365 nm radiation in a photo reactor were evaluated against E. coli, S. epidermis, and S. aureus. The results are dramatic, after exposure of 30 min, significant kills of each bacteria occurred under very low concentration of the compounds (FIGS. 26-28) while higher concentrations were needed for dark killing.

To verify that microtubes don't affect biocidal activity or the compounds, parallel control experiments with quartz cuvette were carried out. It turned out that there was no considerable difference between two systems. Time course experiments for each chemical have been done, for control experiments, irradiation does not have evident influence to E.coli and S.epidermis, but there are significant kills for S. aureus over time, which is consistent with literature reports.

Figure 26:
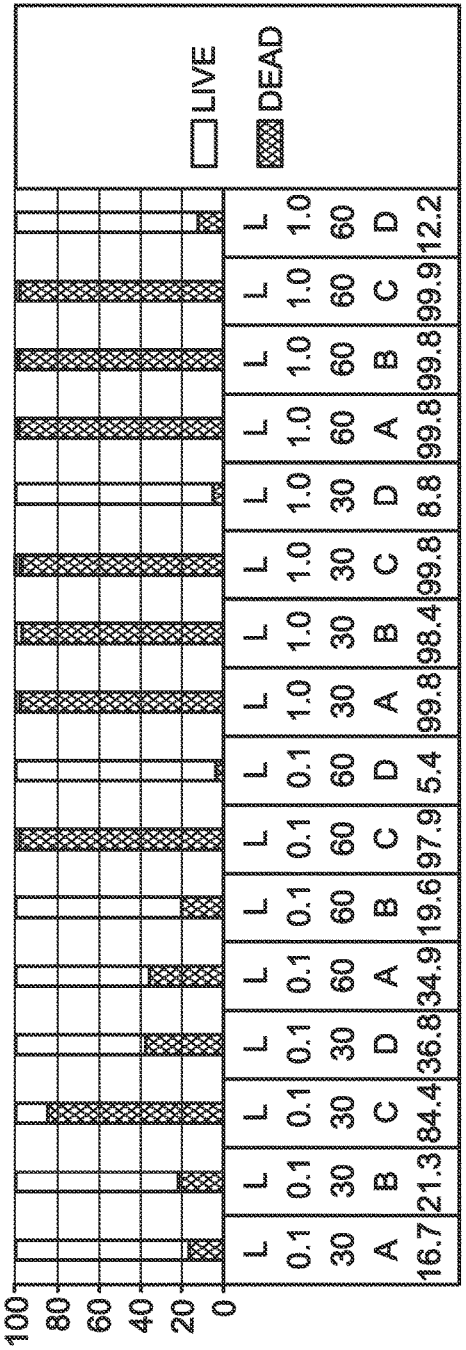
FIG. 26 is a graph of EO-OPE-1 (C3, A), EO-OPE-1 (C2, A), EO-OPE-1 (C3, S), and EO-OPE-1 (Th, C3, A) against *E.coli* with irradiation over 30 min and 60 min. The vertical axis represents the ratio of killed *E.coli*. For the X axis, 1st row—light, 2nd row—concentration (µg/mL), 3rd row—time (min), 4th row—chemicals, 5th row—dead ratio (%).
Figure 27:
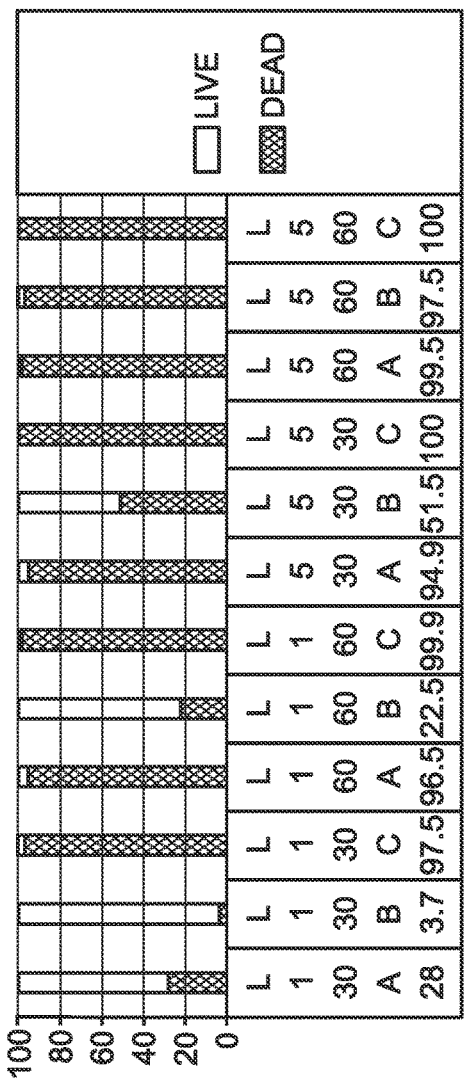
FIG. 27 is a graph of EO-OPE-1 (C3, A), EO-OPE-1 (C2, A), and EO-OPE-1 (C3, S), against *S.epidermis* with irradiation over 30 min and 60 min. The vertical axis represents the ratio of killed *S.epidermis*. For the X axis, 1st row—light, 2nd row—concentration (µg/mL), 3rd row—time (min), 4th row—chemicals, 5th row—dead ratio (%).
Figure 28:
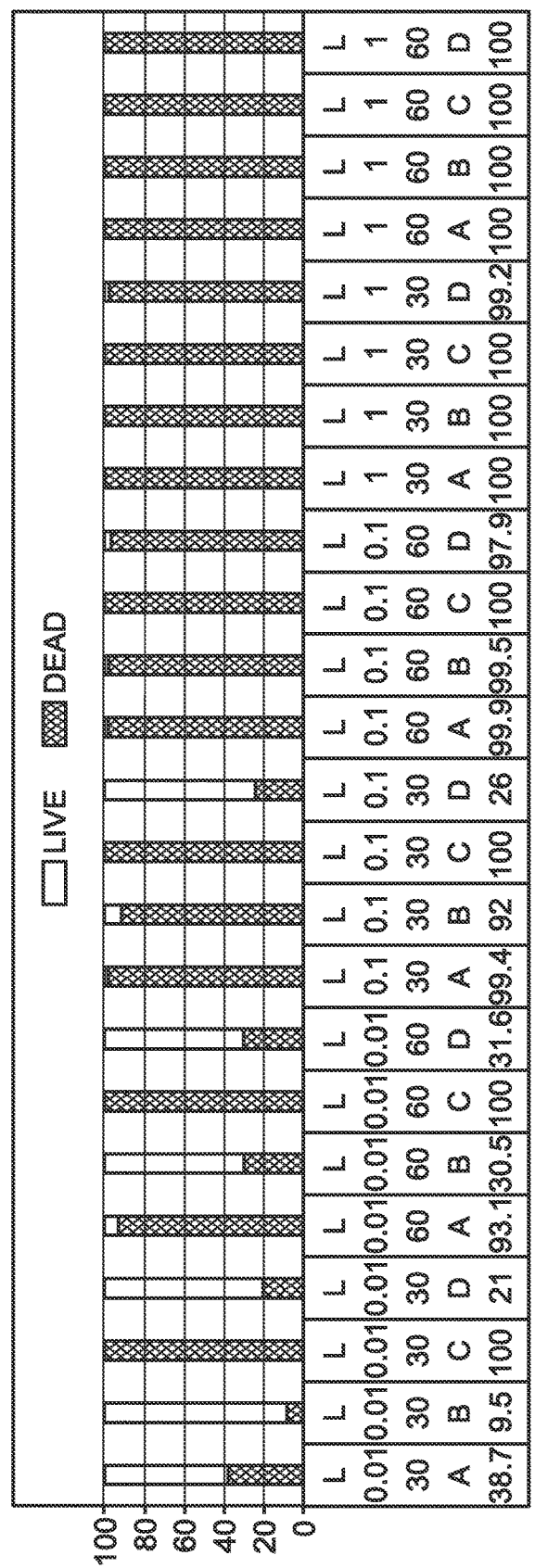
FIG. 28 is a graph of EO-OPE-1 (C3, A), EO-OPE-1 (C2, A), EO-OPE-1 (C3, S), and EO-OPE-1 (Th, C3, A) against *S.aureus* with irradiation over 30 min and 60 min. The vertical axis represents the ratio of killed *S.aureus*. For the X axis, 1st row—light, 2nd row—concentration (µg/mL), 3rd row—time (min), 4th row—chemicals, 5th row—dead ratio (%).

To investigate the dose-dependent and time-dependent effects, various concentrations of each compound were tested over 0 min, 30 min, and 60 min. The results show that higher concentration causes similar or more kills (FIGS. 26-28).

EO-OPE-1(C3, A), EO-OPE-1 (C2, A), EO-OPE-1 (C3, S) and EO-OPE-1 (Th, C3, A) show dramatic light-induced biocidal activity. We have correlated the light-induced biocidal activities and triplet yields of these compounds, and a higher triplet yield suggests a better light-induced biocidal activity. Anionic molecule, EO-OPE-1 (C3, S), exhibits relatively poor light-induced biocidal activity due to Coulombic repulsion which results in decreased amounts of molecules attaching on the surface or inserting in the membrane. We also found that the hydrophobic nature of these compounds plays an important role in the biocidal activity which is consistent with the reported results about nucleic acid stain. This hydrophobicity makes these molecules permeable to bacterial membranes, and $^1O_2$ generates interfacially or inside the membrane by irradiation further damages proteins, nucleic acids or lipids, and therefore, leads to cytotoxicity.

Example II—Biocidal Activity of TM and OPE1-DABCO

Figure 22:
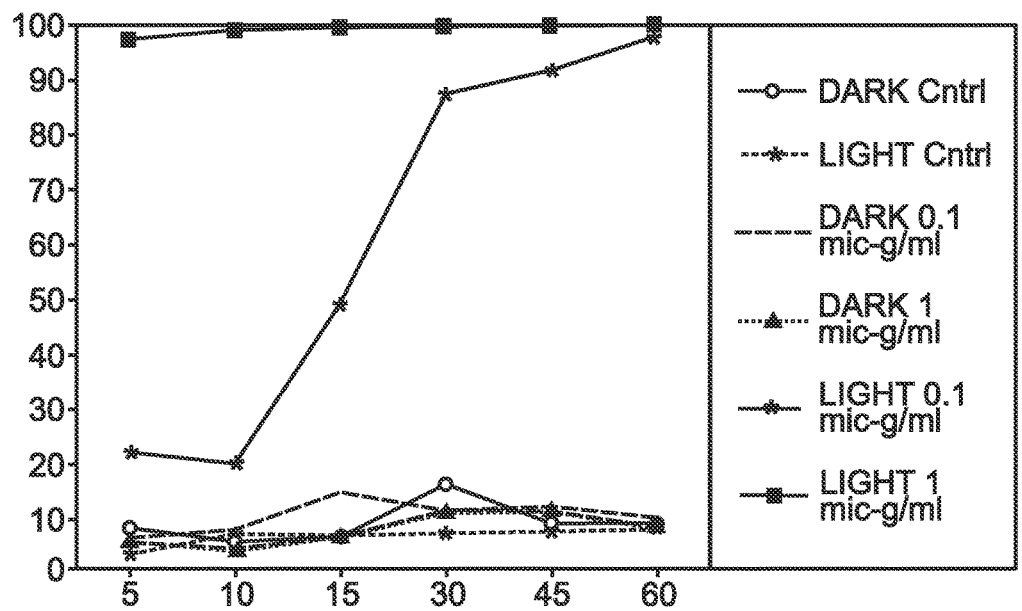
FIG. 22 is a graph showing TM vs. S. Aureus under light and dark conditions at different concentrations and at various time points.
Figure 23:
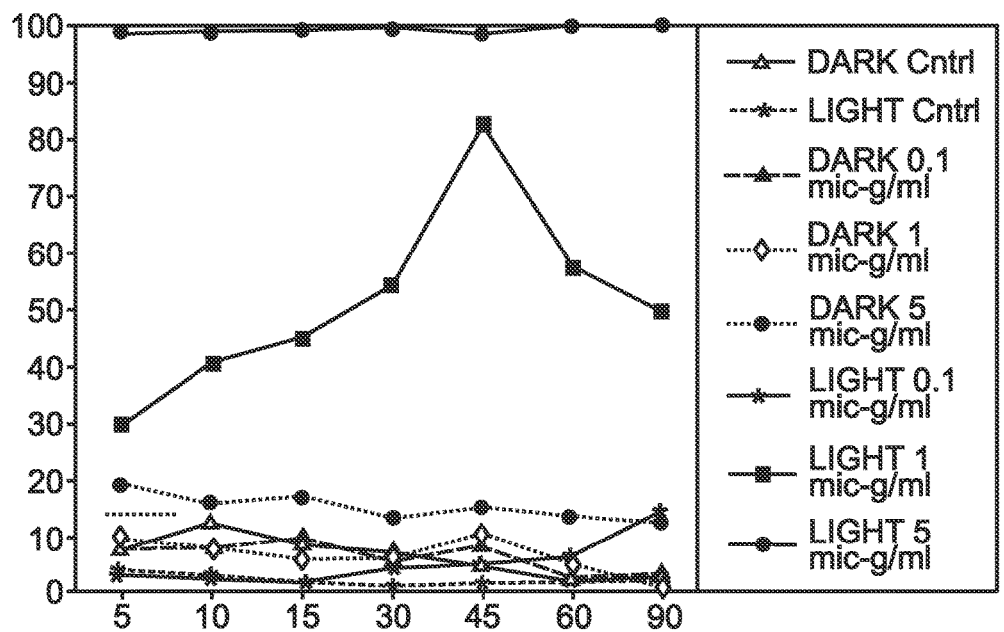
FIG. 23 is a graph showing EO-OPE1-DABCO vs S. Aureus under light and dark conditions at different concentrations and at various time points.
Figure 24:
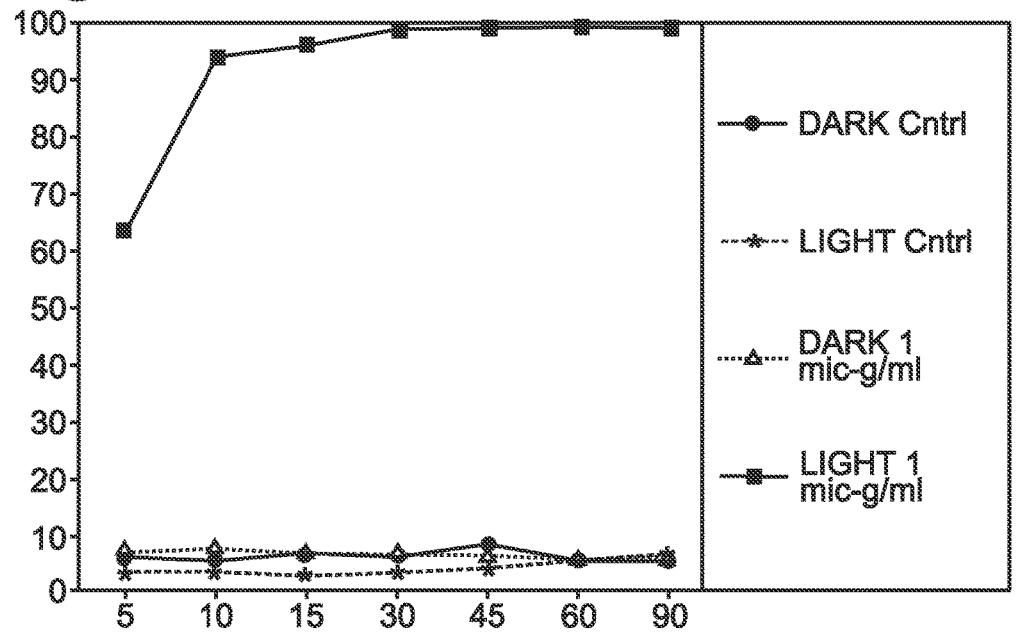
FIG. 24 is a graph showing EO-OPE1-DABCO vs *S. Aureus* under light and dark conditions and at various time points.
Figure 25:
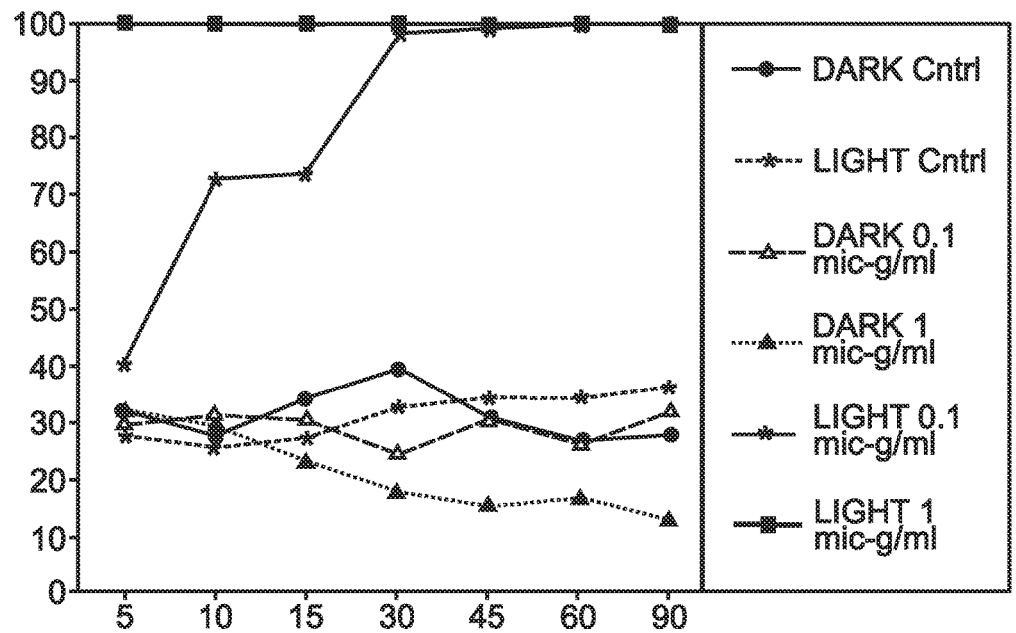
FIG. 25 is a graph showing EO-OPE1-DABCO vs *S. Aureus* under light and dark conditions at different concentrations and at various time points.

Experiments similar to those described in Example 1 above were performed using TM and OPE1-DABCO against S. Aureus. FIG. 22 is a graph showing TM vs. $7 \times 10^7$/mL S. aureus under light and dark conditions at concentrations of 0.1 and 1 μg/mL and at various time points (5, 10, 15, 30, 45, and 60 minutes). FIG. 23 is a graph showing EO-OPE1-DABCO vs $6 \times 10^7$/mL S. aureus under light and dark conditions at different concentrations of 0.1, 1, and 5 μg/mL and at various time points. FIG. 24 is a graph showing EO-OPE1-DABCO vs S. Aureus under light and dark conditions at a concentration of 1 μg/mL and at various time points. FIG. 25 is a graph showing EO-OPE1-DABCO vs S. Aureus under light and dark conditions at different concentrations of 0.1 and 1 μg/mL and at various time points. In all cases, light activated death is clearly demonstrated.

Example III—Antiviral Activity

We investigated the antiviral activity of CPEs and OPEs against MS2 and T4 bacteriophages. Bacteriophage MS2 is a non-enveloped ~27 nm RNA virus with a small genome of ~3600 single strand nucleotides, its morphology is very similar to picornaviruses, such as poliovirus and hepatovirus. Bacteriophage T4 is a relative large non-enveloped DNA virus with a 120 nm long by 86 nm wide head and approximately 100 nm long tail, it has a large genome of ~170 kbp double strand nucleotides. These bacteriophages are commonly employed for studies of environmental pollution and virus detection.

The isoelectric points of MS2 and T4 phage particles are 3.9 and 4~5 respectively, which endow them a slightly negative surface charge in a neutral buffer system, leading to ready association between phage particles and the cationic CPEs/OPEs. Previously we proposed that after exposure to UV-visible light the CPEs/OPEs can generate singlet oxygen followed by the generation of more corrosive reactive oxygen intermediates, because the conjugated pi bonding system within the backbone of CPEs/OPEs allows efficient intersystem crossing energy transfer. $^1O_2$ is known to significantly damage protein, which can account for their high light-activated antiviral ability.

In the current study, investigation of the light-activated and dark antiviral activity of CPEs/OPEs against two model viruses was reported. The destruction effect of CPEs/OPEs on the morphology of bacteriophage was explored by transmission electron microscope (TEM). Sodium dodecyl sulfate-polyacrylamide gel electrophoresis (SDS-PAGE) provided more insights into the light-activated inactivation mechanism.

Experimental Methods

Materials. The antimicrobial molecules were synthesized as described above. Luria broth and Agar were purchased from BD Biosciences. All other chemicals were purchased from Sigma-Aldrich or Alfa Aesar. The model bacteriophages—MS2 and T4 were purchased from the American Type Culture Collection (ATCC) along with their host bacteria, *E. coli* 15577 and *E. coli* 11303. Ultrapure water was used throughout the study (Milli-Q, 18.2 MΩ cm$^{-1}$ resistivity).

Bacteriophage Preparation and Titer. *E. coli* cells were grown in the standard Luria broth. The fresh *E. coli* culture was inoculated from an overnight culture followed by approximately three hours incubation at 37° C. to the exponential growth phase (O.D.$_{600}$~0.5). At this growth phase, the *E. coli* cells were collected by centrifuge and washed with *Escherichia coli* minimal medium (Glucose 5 g/L, Na$_2$HPO$_4$ 6 g/L, KH$_2$PO$_4$ 3 g/L, NH$_4$Cl 1 g/L, NaCl 0.5 g/L, MgSO$_4$, 0.12 g/L, CaCl$_2$ 0.01 g/L, pH 7.2) twice. The cell pellet was resuspended with minimal medium. The phage stock solutions were added into their corresponding bacterial host suspensions the phage-bacteria mixture incubated for 15 minutes at 37° C. for infection. The phage-bacteria mixture was transferred into fresh *Escherichia coli* minimal medium and incubated overnight for viral replication. The phage solution was then centrifuged at 3500 rpm for 10 min, followed by filtering the supernatant with 0.22-μm cellulose ester membrane to remove remaining bacteria and bacterial debris. The phage titer was determined by plaque forming units (PFU). For PFU measurement, the exponential growth phase *E. coli* (ATCC 15597 and 11303 for MS2 and T4 bacteriophage, respectively) cells were incubated with the various dilution tubes of the phage solutions for 15 minutes at 37° C. then added into molten soft LB agar with gentle mixing. The soft agar mixture was then poured onto pre-solidified LB plates. After 6~8 hours incubation, the plaque forming units were counted and phage solutions were diluted to 10$^6$~10$^7$ PFU/ml with the minimal medium for further use.

Phage Inactivation. 10 ug/ml CPEs and OPEs were incubated with model virus solution in the dark or under UV-light for 1 hour. The UV-light irradiation experiments were carried out in a photoreactor (LZC-ORG, Luzchem Research Inc.). Two illumination sources were employed according to the different photophysical properties of CPEs/OPEs. UVA (centered at 350 nm) and LZC-420 (centered at ~420 nm) were used to irradiate OPEs and CPEs respectively. The viral inactivation ability was determined by phage titer as stated above and calculated by log (N$_0$/N), where N is the PFU of the phage solution after exposure to CPEs/OPEs; N$_0$ represents the PFU of corresponding negative control (without CPEs, OPEs or UV-irradiation). The reported values were the average of duplicated measurements.

Transmission Electron Microscopy. High concentration of model viruses (~10$^{11}$ PFU/ml for T4 phage, ~10$^{12}$ PFU/ml for MS2 phage) and CPE/OPE (50 ug/ml) was used for TEM imaging (TEM images were generated in the UNM Electron Microscopy Shared Facility using a Hitachi H7500 transmission electron microscope.) Phage samples were prepared by adding 5 uL phage solutions onto carbon-coated copper grids (freshly cleaned by plasma cleaner) and standing for 2 minutes then rinsing with pure water. The negative stain, 2% aqueous solution of uranyl acetate, was adding onto the grids and standing for 2 minutes, the excess stain was removed by filter paper. The grid was dried in air.

SDS-PAGE. The standard Laemmli protein gel electrophoresis method was used to examine the damage of phage capsid proteins. Electrophoresis was performed at 200V for 30 minutes after which the gels were stained with Coomassie brilliant blue R250 solution for 1 h.

Results and Discussion.

The phage titer assay described herein was done by a series dilution of the phage-CPEs/OPEs mixture and incubating each diluted sample with the corresponding *E. coli* host cells within molten soft LB agar. Since our previous work demonstrated that the CPEs/OPEs can strongly inactive *E. coli* cells, which may interface the plaque assay, it is necessary to study the effect of these residual CPEs/OPEs on the *E. coli* host cells. For the control experiment without phage and CPEs/OPEs, the *E. coli* cells can form a uniform bacterial lawn on the surface of soft agar after 6 hours incubation at 37° C. Under current experimental condition, 0.33 ug/ml was the maximum concentration of CPEs/OPEs within the soft agar, which can not cause any obvious defect on the bacterial lawn at the same condition.

Figure 29:
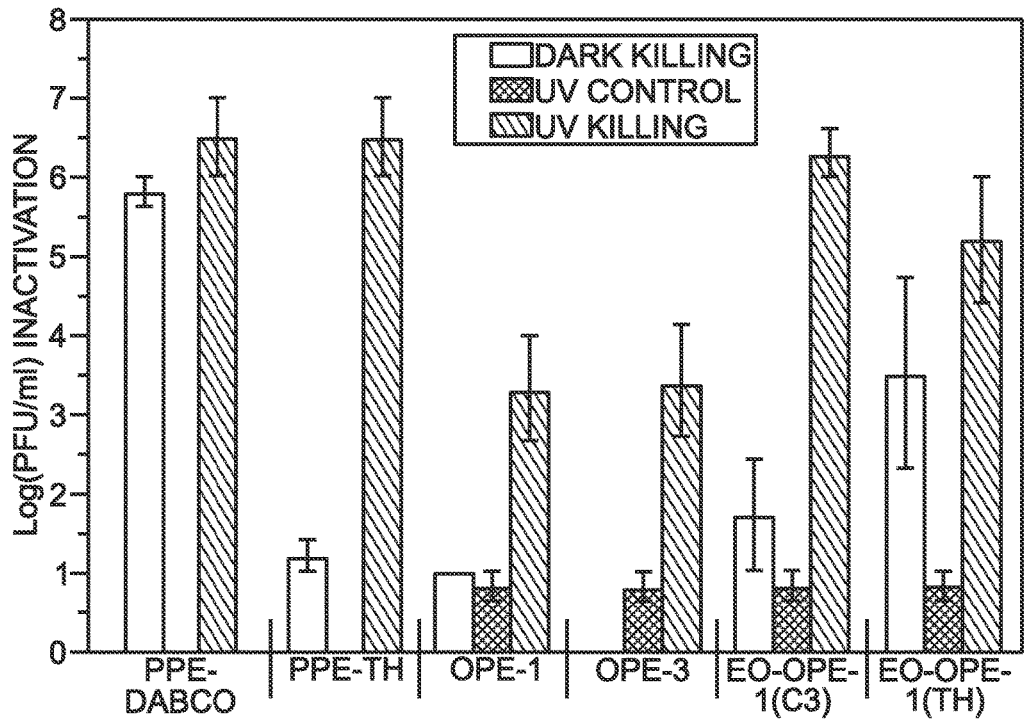
FIG. 29 shows inactivation of bacteriophage MS2 by OPEs in the dark and under UV-light irradiation for 1 hour.
Figure 30:
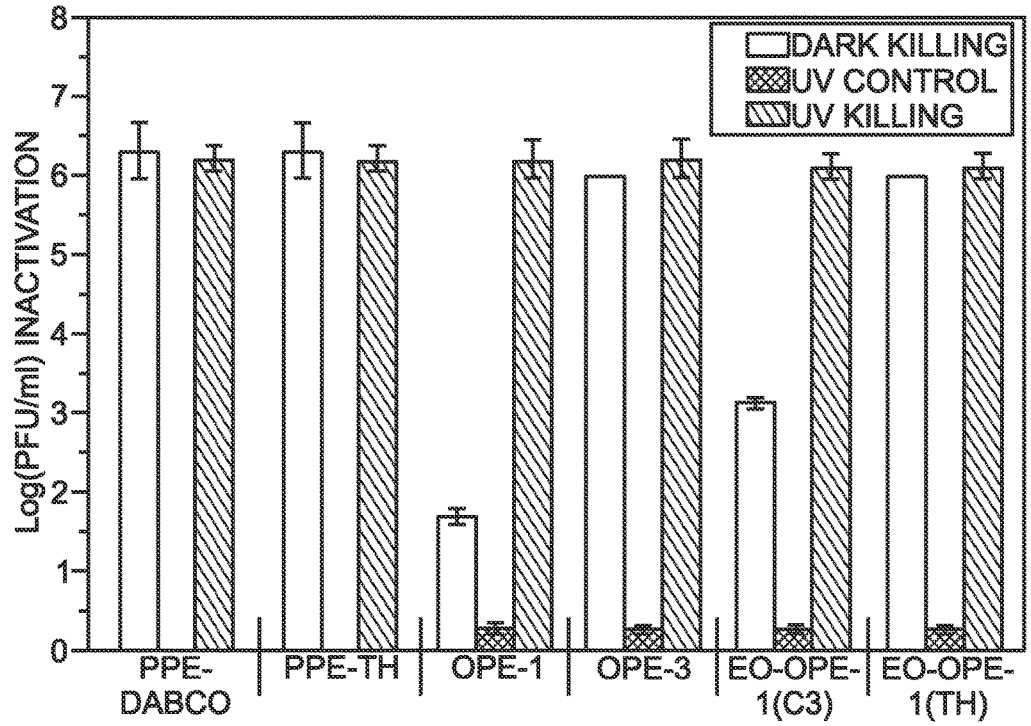
FIG. 30 shows inactivation of bacteriophage T4 by OPEs in the dark and under UV-light irradiation for 1 hour.

Phage Inactivation. FIGS. 29 and 30 depict the phage inactivation under different conditions: CPEs/OPEs in the dark, UV irradiation alone and UV sensitized CPEs/OPEs. PPE-DABCO and EO-OPE-1(Th) exhibit significant dark antiviral activity against T4 phage. PPE-Th, OPE-1 and EO-OPE-1(C3) can inactivate more than 90% T4 phage in the dark. However, no dark inactivation ability was observed for OPE-3 against T4 phage. Enhanced inactivation of T4 phage was observed by CPEs/OPEs in the presence of UV irradiation. Compared with T4 Phage, all of the CPEs/OPEs produce more efficient dark inactivation of MS2; except OPE-1 and EO-OPE-1(C3), all other compounds show more than 6-log inactivation ability against MS2. Meanwhile, enhanced inactivation of MS2 phage was observed by OPE-1 and EO-OPE-1(C3) in the presence of UV irradiation. It is worthwhile to note that the long wavelength UV-visible light (LZC-420) produce negligible inactivation of the model viruses. In contrast, UVA irradiation causes obvious inactivation of T4 phage and moderate inactivation of MS2 phage. The different effects of UVA light on the model viruses can be partially attributed to the following reasons: upon exposure to UVA irradiation, adjacent thymidine residues within T4 phage genome are covalently linked to form thymidine dimmers, leading to the inactivation of T4 phage. In addition, the genome of T4 phage is almost 47 times larger than that of MS2 phage, as a result, T4 phage is more vulnerable to UVA. The T4 bacteriophage infection mechanism has been extensively studied and well established, it recognizes lipopolysaccharide and the OmpC protein on the surface of *E. coli* cell followed by the injection of phage genome into the host cell and replication of phage particle.[9] However, the infection mechanism of MS2 phage is not quite clear, it is believed that the pilus of *E. coli* cell are the receptors for MS2 phage. It is reasonable to propose that the CPEs and OPEs can associate with the model viruses through electrostatic interaction followed by the damage of viral capsid and/or the inhabitation the binding of viral particle towards host *E. coli* cell, upon the direct contact between these compounds and model viruses. According to our previous work, the enhanced antiviral activity of these compounds in the presence of UV-light can be proposed to the generation of corrosive reactive oxygen species after exposure to UV-visible light, which can strongly damage biomolecules. Subsequent results confirm the damage of viral capsid caused by PPE-DABCO and EO-OPE-1(Th).

Figure 31:
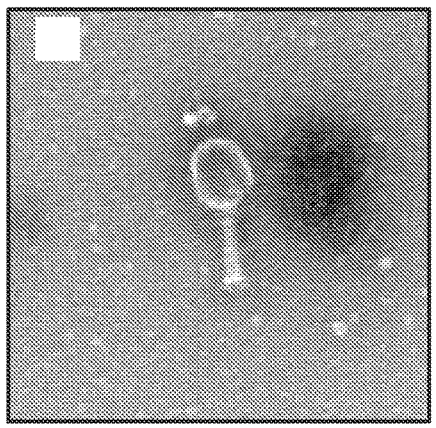
FIG. 31 is a TEM image of uranyl acetate negatively stained model T4 virus alone.
Figure 32:
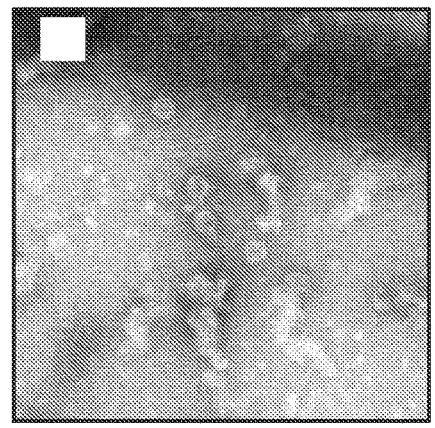
FIG. 32 is a TEM image of uranyl acetate negatively stained model MS2 virus alone.
Figure 33:
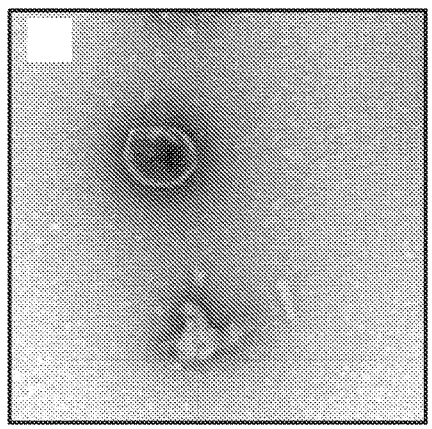
FIG. 33 is a TEM image of uranyl acetate negatively stained T4 phage with PPE-DABCO, dark.
Figure 34:
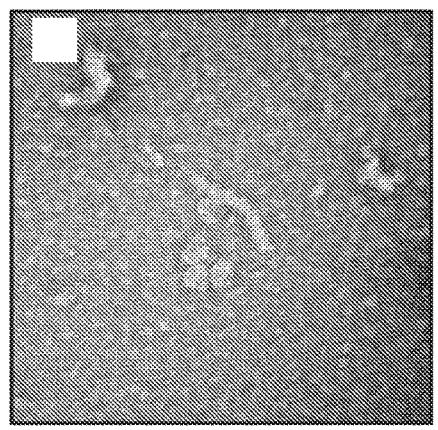
FIG. 34 is a TEM image of uranyl acetate negatively stained MS2 phage with PPE-DABCO, dark.
Figure 35:
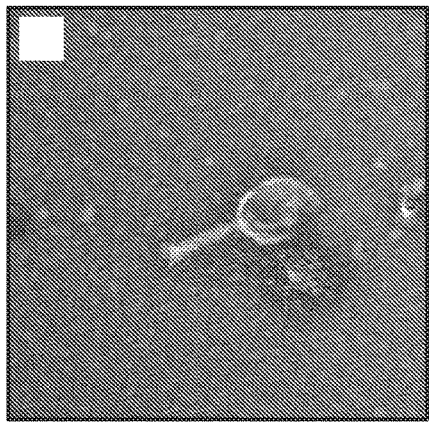
FIG. 35 is a TEM image of uranyl acetate negatively stained T4 phage with PPE-DABCO, LZC-420.
Figure 36:
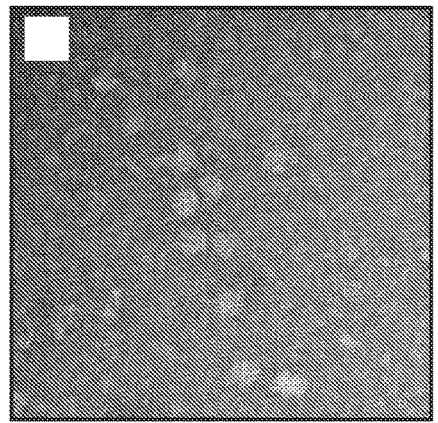
FIG. 36 is a TEM image of uranyl acetate negatively stained MS2 phage with PPE-DABCO, LZC-420.
Figure 37:
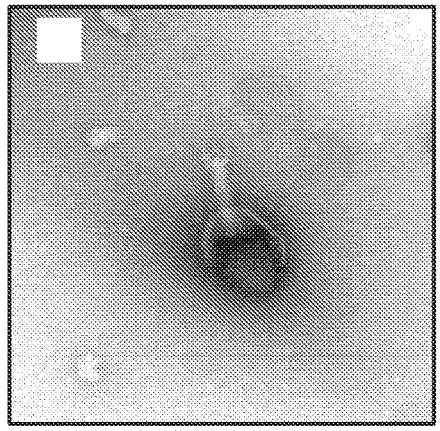
FIG. 37 is a TEM image of uranyl acetate negatively stained T4 phage with EO-OPE(Th), dark.
Figure 38:
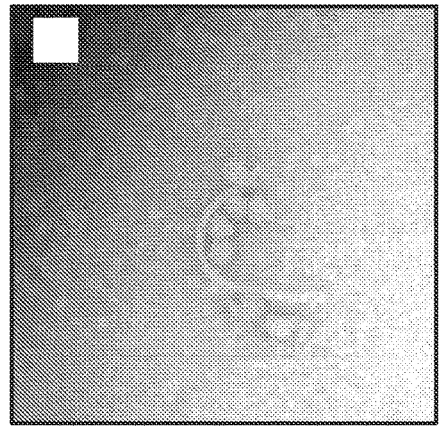
FIG. 38 is a TEM image of uranyl acetate negatively stained MS2 phage with EO-OPE(Th), dark.
Figure 39:
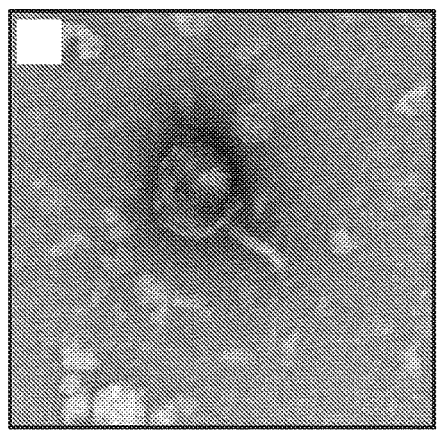
FIG. 39 is a TEM image of uranyl acetate negatively stained T4 phage with EO-OPE(Th), UVA.
Figure 40:
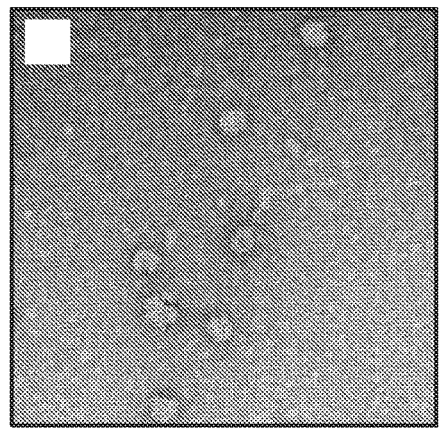
FIG. 40 is a TEM image of uranyl acetate negatively stained MS2 phage with EO-OPE(Th), UVA.

Viral Morphology Damage. To visualize the viral morphology damage by PPE-DABCO and EO-OPE-1(Th), samples immobilized on carbon-coated grids were imaged by TEM, as shown in FIGS. 31-40. More than 10 images were taken for each sample to guarantee the reproducibility of the observed viral damage. The untreated T4 phage maintains its classic morphology with intact head and tail structure (FIG. 31). In contrast, serious damage happens to the PPE-DABCO and EO-OPE-1(Th) treated T4 phage (FIGS. 33, 35, 37, and 39). Likewise, the shape of the intact MS2 phage is uniform and the size is very close to the literature report value (FIG. 32). Obvious morphology change observed for the PPE-DABCO and EO-OPE-1(Th) treated MS2 phage, which are withered and formless (FIGS. 34, 36, 38 and 40). Even though not conclusive, ample amounts of doubtful PPE-DABCO and EO-OPE-1(Th) aggregates are visible close to MS2 and T4 phages (data not shown), which imply the efficient association between CPEs/OPEs and model viruses.

Example IV—Antimicrobial Activity

The activity of PPE-DABCO against *S. cerevisiae* was examined. *S. cerevisiae* was cultured, counted by a coulter counter and diluted $10^7$ mL$^{-1}$ in PBS. The suspended culture was then exposed to 0.13 mM PPE-DABCO for 30 minutes while irradiating with Fiber-Lite 190 and then stained with SYTO 9 and PI (Fungalight™) for 30 minutes. Flow cytometry was then used to count percentage of dead yeast. A control sample (*S. cerevisiae* without exposure to PPE-DABCO) showed 10% dead while the treated samples showed 29-30% dead.

What is claimed is:

1. A material incorporating an oligo-(phenylene ethynylene), wherein the oligo-(phenylene ethynylene) is grafted thereto by chemisorption or wherein the positively charged polymer attaches to a negatively charged surface by physisorption, wherein the oligo-(phenylene ethynylene) has the structure:

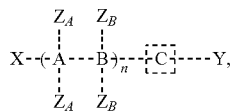

wherein:
n is selected from the group consisting of 1, 2, 3 and 4;
A is selected from the group consisting of $C_2C_6H_2$ and $C_2C_4S$;
B=$C_2C_6H_2$;
C= is either $C_6H_4$ or not present;
X is selected from the group consisting of: $COOCH_2CH_3$, $O(CH_2)_kN(CH_3)_3^+$, $O(CH_2)_kSO_3^-$, and $O(CH_2)_k(C_6H_{12}N_2)C_6H_{13}$;
Y is selected from the group consisting of: $COOCH_2CH_3$, $O(CH_2)_kN(CH_3)_3^+$, $O(CH_2)_kSO_3^-$, $C_6H_2(OCH_3)_3$, and $O(CH_2)_k(C_6H_{12}N_2)C_6H_{13}^{2+}$;
k is selected from the group of whole numbers from 1 to 10;
$Z_A$ is selected from the group consisting of H and $O(CH_2)_j(C_6H_{12}N_2)C_6H_{13}^{2+}$; where j is selected from the group of whole numbers from 1 to 10; and
$Z_B$=H;
wherein:
if X=$COOCH_2CH_3$ and Y=$COOCH_2CH_3$, then A=B=$C_2C_6H_2$, C is $C_6H_4$, and $Z_A$ is $O(CH_2)_k(C_5H_{12}N_2)C_6H_{13}^{2+}$;
if $Z_A$ is H, A is $C_2C_6H_2$, X=$O(CH_2)_kN(CH_3)_3^+$, and C=$C_6H_4$, then Y is selected from the group consisting of $COOCH_2CH_3$, $O(CH_2)_kSO_3^-$, $C_6H_2(OCH_3)_3$, and $O(CH_2)_k(C_6H_{12}N_2)C_6H_{13}^{2+}$;

if $Z_A$ is H, A is $C_2C_6H_2$, X=$O(CH_2)_kN(CH_3)_3^+$, C=$C_6H_4$, and B=$C_2C_6H_2$, then k is selected from the group consisting of 1, 2, 4, 5, 6, 7, 8, 9, and 10;
if $Z_A$ is H, A is $C_2C_6H_2$, X=$O(CH_2)_kN(CH_3)_3^+$, and C is not present, then Y=$C_6H_2(OCH_3)_3$;
if $Z_A$ is H, A is $C_2C_6H_2$ and X=$O(CH_2)_kSO_3^-$, then C=$C_6H_4$ and Y=$O(CH_2)_kSO_3^-$;
if $Z_A$ is H, A is $C_2C_6H_2$, and X=$O(CH_2)_k(C_5H_{12}N_2)C_6H_{13}^{2+}$, then C=$C_6H_4$ and Y=$O(CH_2)_k(C_6H_{12}N_2)C_6H_{13}^{2+}$;
if A is $C_2C_4S$, then C=$C_6H_4$ and X is selected from the group consisting of $O(CH_2)_kN(CH_3)_3^+$ and $O(CH_2)_k(C_6H_{12}N_2)C_6H_{13}^{2+}$;
if X is $O(CH_2)_k(C_6H_{12}N_2)C_6H_{13}^{2+}$, then Y=$O(CH_2)_k(C_6H_{12}N_2)C_6H_{13}^{2+}$;
wherein both the oligo-(phenylene ethynylene) and the material incorporating the same have biocidal, antiviral, and antifungal properties.

2. The material of claim 1 wherein $Z_A$=$O(CH_2)_j(C_6H_{12}N_2)C_6H_{13}^{2+}$; A and B=$C_2C_6H_2$, C=$C_6H_4$, and X and Y=$COOCH_2CH_3$.

3. The material of claim 2 wherein j=3.

4. The material of claim 1 wherein A and B=$C_2C_6H_2$, C=$C_6H_4$, and X and Y=$O(CH_2)_kN(CH_3)_3^+$.

5. The material of claim 4 where k=2.

6. The material of claim 1 wherein A and B=$C_2C_6H_2$, C=$C_6H_4$, and X and Y=$O(CH_2)_3SO_3^-$.

7. The material of claim 1 wherein A=$C_2C_4S$, B=$C_2C_6H_2$, C=$C_6H_4$, and X and Y=$O(CH_2)_3N(CH_3)_3^+$.

8. The material of claim 1 wherein A and B=$C_2C_6H_2$, C is not present, X=$O(CH_2)_3N(CH_3)_3^+$ and Y=$C_6H_2(OCH_3)_3$.

9. The material of claim 1 wherein A and B=$C_2C_6H_2$ and C=$C_6H_4$.

10. The material of claim 1 wherein A=$C_2C_4S$, B=$C_2C_6H_2$, and C=$C_6H_4$.

11. The material of claim 1 functionally attached to a material or substance so that the oligo-(phenylene ethynylene) can interfere with the pathogenicity of a pathogen that contacts the oligo-(phenylene ethynylene).

12. The material of claim 1 where k=3.

13. The material of claim 1 wherein the material is a fiber, or a textile formed therefrom.

14. The material of claim 13 wherein the fiber or textile comprises a natural fiber, a synthetic fiber, or both.

15. The material of claim 14 wherein the natural fiber is cotton, silk, or wool, or a blend thereof.

16. The material of claim 14 wherein the synthetic fiber is rayon or nylon.

17. The material of claim 14 wherein the synthetic fiber is produced by electrospinning.

18. The material of claim 13 wherein the fiber or textile is comprised by an object that is potentially contaminated with a microorganism or a virus.

19. The material of claim 18 wherein the object is a wound treatment, a bandage, a swab, a sterile mat, a liner, or a filter for water purification.

20. The material of claim 18 wherein the object is a mattress, a bed linen, a countertop covering, a tablecloth, or a curtain.

21. A material incorporating an oligo-(phenylene ethynylene), wherein the oligo-(phenylene ethynylene) is grafted thereto by chemisorption or wherein the positively charged polymer attaches to a negatively charged surface by physisorption, wherein the oligo-(phenylene ethynylene) has the structure:

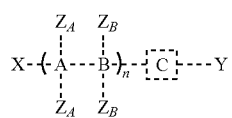

wherein:
n is selected from the group consisting of 1, 2, 3 and 4;
A is selected from the group consisting of $C_2C_6H_2$ and $C_2C_4S$;
$B=C_2C_6H_2$;
C=is either $C_6H_4$ or not present;
X is selected from the group consisting of: $COOCH_2CH_3$, $^-O(CH_2)_2N(CH_3)_3^+$, $O(CH_2)_3N(CH_3)_3^+$, and $O(CH_2)_3SO_3^-$;
Y is selected from the group consisting of: $COOCH_2CH_3$, $^-O(CH_2)_2N(CH_3)_3^+$, $O(CH_2)_3N(CH_3)_3^+$, and $O(CH_2)_3SO_3^-$;
$Z_A$ is H; and
$Z_B$=H;
wherein:
if A is $C_2C_6H_2$, $X=O(CH_2)_3N(CH_3)_3^+$, $C=C_6H_4$, and $B=C_2C_6H_2$, then Y is selected from the group consisting of $COOCH_2CH_3$, and $O(CH_2)_3SO_3^-$;
if A is $C_2C_6H_2$ and $X=O(CH_2)_2N(CH_3)_3^+$ or $O(CH_2)_3N(CH_3)_3^+$, and C is not present, then $Y=C_6H_2(OCH_3)_3$; and
if A is $C_2C_6H_2$ and $X=O(CH_2)_3SO_3^-$ then $C=C_6H_4$ and $Y=O(CH_2)_3SO_3^-$;
wherein
both the oligo-(phenylene ethynylene) and the material incorporating the same have biocidal, antiviral, and antifungal properties, and
the material is a fiber, or a textile formed therefrom.

22. The material of claim 1, wherein the material is a stimuli responsive material.

* * * * *